United States Patent
Park et al.

(10) Patent No.: US 10,182,769 B2
(45) Date of Patent: Jan. 22, 2019

(54) INFORMATION MANAGEMENT METHOD AND ELECTRONIC DEVICE

(71) Applicant: Samsung Electronics Co., Ltd., Suwon-si, Gyeonggi-do (KR)

(72) Inventors: Joeng Sun Park, Seoul (KR); Soon Hwan Kwon, Seongnam-si (KR); Tae Sic Lim, Gumi-si (KR); Jae Geol Cho, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 180 days.

(21) Appl. No.: 14/719,761

(22) Filed: May 22, 2015

(65) Prior Publication Data
US 2015/0335295 A1    Nov. 26, 2015

(30) Foreign Application Priority Data

May 22, 2014    (KR) .................. 10-2014-0061378

(51) Int. Cl.

| | |
|---|---|
| G08C 19/22 | (2006.01) |
| A61B 5/00 | (2006.01) |
| A61B 5/024 | (2006.01) |
| A61B 5/026 | (2006.01) |
| A61B 5/1455 | (2006.01) |
| G06F 19/00 | (2018.01) |
| G16H 40/67 | (2018.01) |

(52) U.S. Cl.
CPC .......... *A61B 5/7285* (2013.01); *A61B 5/0022* (2013.01); *A61B 5/0261* (2013.01); *A61B 5/02416* (2013.01); *A61B 5/14551* (2013.01); *A61B 5/742* (2013.01); *G06F 19/00* (2013.01); *G16H 40/67* (2018.01); *A61B 2560/0266* (2013.01)

(58) Field of Classification Search
None
See application file for complete search history.

(56) References Cited

U.S. PATENT DOCUMENTS

| | | | |
|---|---|---|---|
| 8,718,938 B2 | 5/2014 | Wolf et al. | |
| 9,198,585 B2 | 12/2015 | Lim et al. | |
| 9,220,410 B2 | 12/2015 | Sheynblat et al. | |
| 2005/0064902 A1 | 3/2005 | Goris et al. | |
| 2008/0234935 A1 | 9/2008 | Wolf et al. | |
| 2009/0157429 A1* | 6/2009 | Lee .................. | A61B 5/0002 705/3 |
| 2013/0005310 A1 | 1/2013 | Lim et al. | |

(Continued)

FOREIGN PATENT DOCUMENTS

| | | |
|---|---|---|
| CN | 2539983 Y | 3/2003 |
| CN | 1602026 A | 3/2005 |

(Continued)

*Primary Examiner* — Adolf Dsouza
(74) *Attorney, Agent, or Firm* — Jefferson IP Law, LLP

(57) ABSTRACT

A method for information management of an electronic device and the electronic device therefor are provided. The method includes receiving a trigger signal for activating a sensor configured to receive bio information, activating the sensor according to the received trigger signal, obtaining, by the activated sensor, the bio information corresponding to at least one of an object approaching the sensor or an object contacting the sensor, and outputting the obtained bio information.

18 Claims, 9 Drawing Sheets

(56) References Cited

U.S. PATENT DOCUMENTS

| | | |
|---|---|---|
| 2014/0018635 A1 | 1/2014 | Buchheim et al. |
| 2014/0116133 A1 | 5/2014 | Sheynblat et al. |
| 2014/0164611 A1* | 6/2014 | Molettiere ........... A61B 5/6838 709/224 |
| 2015/0120320 A1* | 4/2015 | Fateh .................... G06Q 50/22 705/2 |
| 2015/0173617 A1 | 6/2015 | Sheynblat et al. |

FOREIGN PATENT DOCUMENTS

| | | |
|---|---|---|
| CN | 1964369 A | 5/2007 |
| CN | 201194798 Y | 2/2009 |
| CN | 101515952 A | 8/2009 |
| CN | 101636637 A | 1/2010 |
| CN | 102846314 A | 1/2013 |
| CN | 103431850 A | 12/2013 |
| RU | 2521104 C2 | 6/2014 |

\* cited by examiner

INFORMATION MANAGEMENT METHOD AND ELECTRONIC DEVICE

CROSS-REFERENCE TO RELATED APPLICATION(S)

This application claims the benefit under 35 U.S.C. § 119(a) of a Korean patent application filed on May 22, 2014 in the Korean Intellectual Property Office and assigned Serial number 10-2014-0061378, the entire disclosure of which is hereby incorporated by reference.

TECHNICAL FIELD

The present disclosure relates to an information management.

BACKGROUND

Electronic devices such as smartphones and tablets provide various useful functions to users through various applications. The electronic device may provide menus or icons in relation to function management.

The above-mentioned electronic devices require menu or icon list activation of an electronic device in relation to a specific function management that users want to use, menu or icon search corresponding to a specific function, and various input controls relating to a found function. In such a way, electronic devices require complex procedures regardless of an overall management of a corresponding function or some management of entire functions in relation to function management.

The above information is presented as background information only to assist with an understanding of the present disclosure. No determination has been made, and no assertion is made, as to whether any of the above might be applicable as prior art with regard to the present disclosure.

SUMMARY

Embodiments of the present disclosure are to address at least the above-mentioned problems and/or disadvantages and to provide at least the advantages described below. Accordingly, an embodiment of the present disclosure is to provide a method and device for easy and simple specific sensor management.

Another embodiment of the present disclosure is to provide a method and device for simplifying procedure processing relating to a partial management of a specific function.

Another embodiment of the present disclosure is to provide a method and device for supporting an entire management relating to a partial management of a specific function.

Another embodiment of the present disclosure is to provide a method and device for easy information management occurring from a partial management or an entire management of a specific function on the basis of device related information or user input information.

In accordance with an embodiment of the present disclosure, an information management method is provided. The method includes receiving a trigger signal for activating a sensor related to a bio information, activating the sensor when the trigger signal is detected, obtaining bio information corresponding to one of an approached object or a contacted object by using the activated sensor, and outputting the obtained bio information.

In accordance with another embodiment of the present disclosure, an electronic device is provided. The device includes an information management module configured to obtain, when a trigger signal for activating a sensor related to a bio information is detected, bio information on one of an approached object or a contacted object by activating the sensor and a display configured to output the obtained bio information.

Other embodiments, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other embodiments, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
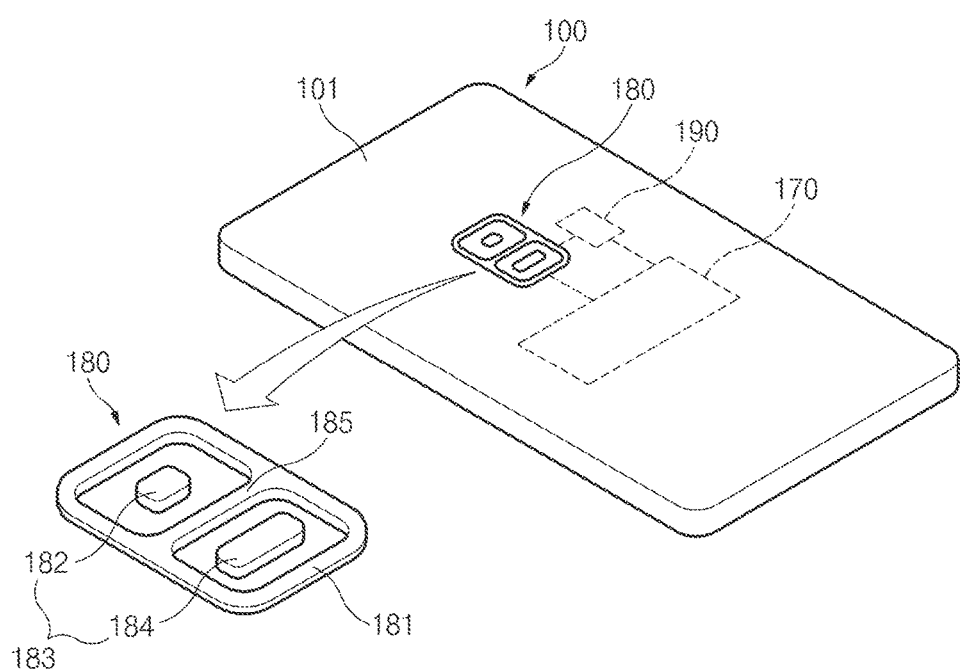
FIG. 1 is a view illustrating an electronic device relating to information management according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The expression "include," "comprise," "including," or "comprising," used in various embodiments of the present disclosure specifies a corresponding function, operation or component but does not limit at least one additional function, operation, or component. Additionally, the term "include," "comprise," "including," or "comprising," specifies features, numbers, processes, components, parts, or combinations thereof but does not exclude other features, numbers, processes, components, parts, or combinations thereof.

In various embodiments of the present disclosure, the expression "A or B" or "at least one of A or/and B" may include all possible combinations of items listed together. For instance, the expression "A or B", or "at least one of A or/and B" may indicate include A, B, or both A and B.

The expressions such as "1st", "2nd", "first", "second", and the like used herein may modify various different elements of various embodiments, but do not limit the elements. For instance, such expressions do not limit the order and/or importance of corresponding components. The expressions may be used to distinguish one element from another element. For instance, both "a first user device" and "a second user device" indicate a user device but indicate different user devices from each other. For example, a first component may be referred to as a second component and vice versa without departing from the scope of the present disclosure.

When one part (or element, device, and the like) is referred to as being "connected" to another part (or element, device, and the like), it should be understood that the former can be "directly connected" to the latter, or "connected" to the latter via an intervening part (or element, device, and the like). In contrast, when an element is referred to as being "directly connected" or "directly coupled" to another element, there are no intervening elements present.

In various embodiments of the present disclosure, terms used in this specification are used to describe specific embodiments, and are not intended to limit the scope of the present disclosure. The terms of a singular form may include plural forms unless they have a clearly different meaning in the context.

Unless indicated herein, all the terms used herein, which include technical or scientific terms, may have the same meaning that is generally understood by a person skilled in the art. In general, the terms defined in the dictionary should be considered to have the same meaning as the contextual meaning of the related art, and, unless clearly defined herein, should not be understood abnormally or as having an excessively formal meaning.

An electronic device according to various embodiments of the present disclosure may be a device supporting sensor management. For instance, electronic devices may include at least one of smartphones, tablet personal computers (PCs), mobile phones, video phones, electronic book (e-book) readers, desktop personal computers (PCs), laptop personal computers (PCs), netbook computers, personal digital assistants (PDAs), portable multimedia player (PMPs), Moving Picture Experts Group (MPEG-1 or MPEG-2) Audio Layer III (MP3) players, mobile medical devices, cameras, and wearable devices (e.g., head-mounted-devices (HMDs) such as electronic glasses, electronic apparel, electronic bracelets, electronic necklaces, electronic appcessories, electronic tattoos, and smart watches).

According to various embodiments, an electronic device may be smart home appliances supporting sensor management. The smart home appliances may include at least one of, for example, televisions, digital video disk (DVD) players, audios, refrigerators, air conditioners, cleaners, ovens, microwave ovens, washing machines, air cleaners, set-top boxes, TV boxes (e.g., Samsung HomeSync™, Apple TV™ or Google TV™), game consoles, electronic dictionaries, electronic keys, camcorders, and electronic picture frames.

According to various embodiments, an electronic device may include at least one of various medical devices (e.g., magnetic resonance angiography (MRA) devices, magnetic resonance imaging (MRI) devices, computed tomography (CT) devices, medical imaging devices, ultrasonic devices, and the like), navigation devices, global positioning system (GPS) receivers, event data recorders (EDRs), flight data recorders (FDRs), vehicle infotainment devices, marine electronic equipment (e.g., marine navigation systems, gyro compasses, and the like), avionics, security equipment, and industrial or household robots.

According to various embodiments, an electronic device may include at least one of furniture or buildings/structures supporting sensor management, electronic boards, electronic signature receiving devices, projectors, and various measuring instruments (e.g., water, electricity, gas, or radio signal measuring instruments). In various embodiments of the present disclosure, an electronic device may be one of the above-mentioned various devices or a combination thereof. Furthermore, it is apparent to those skilled in the art that an electronic device according to various embodiments of the present disclosure is not limited to the above-mentioned devices.

Hereinafter, an electronic device according to various embodiments will be described in more detail with reference to the accompanying drawings. The term "user" in various embodiments may refer to a person using an electronic device or a device using an electronic device (e.g., an artificial intelligent electronic device).

FIG. 1 is a view illustrating an electronic device relating to information management according to various embodiments of the present disclosure.

Referring to FIG. 1, an electronic device 100 may include a body part 101, a sensor module 180, and an information management module 170. Additionally, or alternatively, the electronic device 100 may further include a sensor processor 190 (or a sensor hub).

The electronic device 100 may collect (or obtain) user bio information by using the sensor module 180 disposed at one side of the body part 101. For example, the electronic device 100 may collect bio information such as user's heart rate information, oxygen saturation information, blood flow information, and pulse save information by using the sensor module 180. The electronic device 100 may output the collected bio information through a display.

The electronic device 100 may support to selectively process a partial management (e.g., a bio information collection and output function) and an entire management (e.g., health related service information offer provided based on bio information, health schedule management according to bio information accumulation, and bio information based patient management service) while bio information related to various applications are installed. For example, when a specified event occurs, the electronic device 100 may recognize a corresponding event as a trigger signal relating to bio information collection and may determine whether user bio information collection is available by managing the sensor module 180. When it is determined that the bio information collection is available, the electronic device 100 may support bio information collection and output by using the sensor module 180. During this operation, the electronic device 100 may not manage an entire function (e.g., an entire function relating to bio information collection, output, store, or transmission) relating to the bio information collection but may support only a bio information collection and output function. In relation to this, the electronic device 100 may support a corresponding function on the basis of a program module prepared to support a partial function for supporting only a bio information collection or output function.

Additionally or alternatively, when a request relating to bio information store occurs, the electronic device 100 may accumulate and store bio information on the basis of user index information (e.g., a phone number of an electronic device). The electronic device 100 may provide various bio information related services on the basis of the accumulated stored information. As mentioned above, the electronic device 100 supports a procedure to more easily and simply process a bio information partial management such as bio information check and additionally supports to use bio information related various services simply. During this operation, the electronic device 100 may manage a program module prepared to manage an entire bio information related function. Alternatively, the electronic device 100 may manage a program module for receiving bio information to store or transmit the bio information according to a program module management relating to a bio information collection or output function.

The body part 101, for example, may have a predetermined thickness and width and may be formed of at least one material of metal and non-metal. Various electronic device components (e.g., an information management module 170, a sensor processor 190, a processor, and a printed circuit board) may be disposed in the body part 101. According to an embodiment, a display may be disposed at the front of the body part 101. The display may display various information relating to a sensor module 180 management. The sensor module 180 may be disposed at one side, for example, the rear, of the body part 101. According to various embodiments, the sensor module 180 may be disposed on at least one of a side part (e.g., at least one of the top/bottom/left/right sides) and a font part (e.g., at least one area of display edges).

As mentioned above, the sensor module 180 may be disposed on at least one position in one side of the body part 101. As shown in the drawing, one sensor module 180 is disposed at the rear upper center part of the body part 101. According to an embodiment, the sensor module 180 may include a specific sensor (e.g., a heart rate sensor including a light emitting unit 182 or a photodiode 184) relating to bio information collection. The light emitting unit 182 may emit light of a given specific frequency band. The photodiode 184 collects the light emitted from the light emitting unit 182. The photodiode 184 may measure the received light amount to provide the measured received light to at least one of the sensor processor 190 and the information management module 170 of the electronic device 100. According to an embodiment, a body part such as a user's finger may be disposed to cover the sensor module 180 area where the heart rate sensor 183 including the light emitting unit 182 and the photodiode 184 is disposed. During this state, the light emitted from the light emitting unit 182 may penetrate a user body part and be reflected to be delivered to the photodiode 184.

According to various embodiments, the sensor module 180 may include the heart rate sensor 183 (e.g., the light emitting unit 182 and the photodiode 184) and a guard 185. The guard 185 may be disposed with a predetermined height and width between the light emitting unit 182 and the photodiode 184. The guard 185 may serve to prevent the light emitted from the light emitting unit 182 from being directly emitted to the photodiode 184. The guard 185 may have a size of more than the height of a lamp that forms the light emitting unit 182. Accordingly, as light among lights emitted from the light emitting unit 182 passes through a user body part and is delivered to the photodiode 184, the sensor module 180 may support a more accurate bio information acquisition.

According to various embodiments, the sensor module 180 may include the heart rate sensor 183 (e.g., the light emitting unit 182 and the photodiode 184), the guard 185, or a specific sensor (e.g., a touch sensor 181) relating to a trigger signal collection. The touch sensor 181 may be disposed to surround at least one of the light emitting unit 182, the photodiode 184, and the guard 185. As shown in the drawing, the touch sensor 181 is disposed to surround the entire light emitting unit 182, photodiode 184, and guard 185. According to various embodiments, the touch sensor 181 may be disposed to surround at least one of the light emitting unit 182, the photodiode 184, and the guard 185. Alternatively, the touch sensor 181 may be disposed in an adjacent area within a specified distance of the light emitting unit 182, the photodiode 184, and the guard 185. The touch sensor 181 may perform a trigger role for detecting that at least part of a user' body contacts the sensor module 180. When a user body part is in contact, the touch sensor 181 may deliver an event (e.g., a trigger signal) corresponding thereto to at least one of the sensor module 180, the sensor processor 190, and the information management module 170.

According to various embodiments, the touch sensor 181 may include at least one of a resistive sensor for detecting the case that a pressure of more than a predetermined magnitude is provided, a capacitive sensor for detecting changes in capacity amount, a current change detection sensor for detecting a current change according to the contact of an organism, a switch type sensor for connecting separated contact points as a pressure of more than a predetermined magnitude is provided, and a proximity sensor for receiving an electrical change according to the proximity of an object. The above-mentioned touch sensor 181 or various sensors may generate a trigger signal (e.g., an event corresponding to a pressure detection of a predetermined magnitude, an event corresponding to an electrical change detection, and an event corresponding to a physical change detection) relating to the activation of the sensor module 180 according to the approach, contract, or pressing. The generated trigger signal may be delivered to at least one of the sensor module 180, the sensor processor 190, and the information management module 170. According to various embodiments, in relation to the collection of a trigger signal, the sensor module 180 not including the touch sensor 181 may perform the light emission of the light emitting unit 182 at a specified period in correspondence of a control of the information management module 170. In this case, the trigger signal may include the case that a light change amount collected by the photodiode 184 has a specified change value.

The information management module 170 may control the light emitting unit 182, the photodiode 184, or the touch sensor 181 included in the sensor module 180. According to an embodiment, the information management module 170 may determine an electrical change according to an object approach or contact by supplying power of the electronic device 100 to the touch sensor 181. When an electrical change is greater than a specified value, the information management module 170 may activate the sensor module 180 to determine whether the object is a user's body part. For example, the information management module 170 may determine a sensor signal (e.g., a light change amount) collected by the sensor module 180 to determine whether the sensor signal corresponds to a specified value (e.g., a light change amount corresponding to the contact of a user finger). When the specified value is received from the sensor module 180, the information management module 170 may control a sensor module 180 control for bio information (e.g., heart rate information) detection. For example, the information management module 170 may control a light emitting relating to a heart rate information detection. The information management module 170 may control output of a result of the collected bio information through a display.

According to an embodiment, when a specified electrical change is not received from the touch sensor 181, the information management module 170 may maintain the object approach or contact detection of the touch sensor 181. When the sensor module 180 is activated, the information management module 170 may deactivate the touch sensor 181. Additionally, while a user body part determine is performed by the sensor module 180, the information management module 170 may deactivate the touch sensor 181. When a user body part contact (e.g., a user finger contact) is determined, the information management module 170 may control bio information collection by using the sensor module 180 while performing a control to maintain a deactivation state of the touch sensor 181. When there is no user body part contact, the information management module 170 may deactivate the sensor module 180. Then, the information management module 170 may change the touch sensor 181 into an activation state. During this operation, when a deactivation and activation operation of the touch sensor 181 occur repeatedly more than a predetermined number of times for a specified time, the information management module 170 may deactivate the touch sensor 181 or change an activation period of the touch sensor 181 for a specified time.

According to various embodiments, when a sensor signal corresponding to an object approach or contact instead of a user body part is received from the sensor module 180 after the deactivation of the touch sensor 181, the information management module 170 may deactivate the touch sensor 181. The information management module 170 may determine whether there is an object approach or contact by activating the touch sensor 181 after a predetermined time elapses. When an object approach or contact instead of a user body part occurs after a predetermined time elapses, the information management module 170 may adjust (e.g., increase a touch sensor 181 deactivation time size) a specified time. When it is determined that a user body part approaches or contacts, the information management module 170 may initialize an activation period or deactivation period of the touch sensor 181. The information management module 170 may apply an activation or deactivation period change of the touch sensor 181 to at least one of various sensors relating to a bio information collection of the sensor module 180.

The information management module 170 may determine whether a sensor signal corresponding to a specified reference value (e.g., a light change amount corresponding to an object approach or contact) is collected while managing the light emitting unit 183 of the sensor module 180 with a specified period (e.g., a several millisecond or several second period). When a sensor signal corresponding to a specified reference value is collected, the information management module 170 may determine whether a corresponding object is a user body part. When a corresponding object is a user body part, the information management module 170 may control a sensor module 180 management for bio information detection.

According to various embodiments, when a sensor signal corresponding to a specified reference value is not collected, the information management module 170 may manage the sensor module 180 with a specified period to detect an object approach or contact. When a sensor signal corresponding to a specified reference value is collected, the information management module 170 may use the sensor module 180 to determine whether there is a user body part approach or contact. When a sensor signal value provided from the sensor module 180 is a specified value (e.g., a sensor signal value corresponding to a user body part approach or contact), the information management module 170 may use the sensor module 180 in order for bio information collection. When a sensor signal value is different from a specified value (e.g., a sensor signal value not corresponding to a user body part approach or contact is received), the information management module 170 may manage the sensor module 180 with a specified period. Alternatively, when a sensor signal value is different from a specified value, the information management module 170 may deactivate the sensor module 180 for a specified time. The information management module 170 may activate the sensor module 180 after the specified time elapses. Alternatively, when an object (instead of a user body part) approach or contact detection is repeated more than specified times, the information management module 170 may deactivate the sensor module 180 for a specified time.

The sensor processor 190 may be directly connected to the sensor module 180. For example, the sensor processor 190 may be disposed between the sensor module 180 and the processor 120 or between the sensor module 180 and the information management module 170. The sensor processor 190 may include sensor module 180 management related information. The sensor processor 190 may process a control relating to an activation or deactivation of the sensor module 180 separately (or independently) from the processor 120 or the information management module 170. In relation to a trigger signal collection, the sensor processor 190 may maintain a sensor such as the touch sensor 181 to be in a turn-on state or activate or deactivate the sensor at a predetermined period. The sensor processor 190 may activate or deactivate the sensor module 180 in relation to a trigger signal collection of the sensor module 180. When a trigger signal is received, the sensor processor 190 may deliver the trigger to the processor 120 or the information management module 170. On the basis of the above-mentioned operation, the sensor processor 190 may support a partial management of the sensor module 180 while not waking up an application processor (AP) relating to the information management module 170 or the processor 120 in relation to the management of the sensor module 180. According to various embodiments, the sensor processor 190 may be designed to be responsible for the collection of a trigger signal and the output of bio information collected by the sensor module 180.

As mentioned above, when a trigger signal (e.g., a signal that a sensor such as the touch sensor 181 detects an object contact or a signal that the sensor module 180 detects an object contact) is received, the electronic device 100 may manage the sensor module 180 to determine whether the object is a user body. When it is determined that a user body contacts, the electronic device 100 may support a partial management of a function relating to the sensor module 180 for collecting and outputting bio information on the basis of the sensor module 180. According to various embodiments, when an input event relating to a user control (e.g., bio information store or transmission) occurs after bio information output, the electronic device 100 may activate an application relating to bio information. The electronic device 100 may support an entire management of a function relating to the sensor module 180 providing a specific service designated based on an activated application and bio information.

Figure 2:
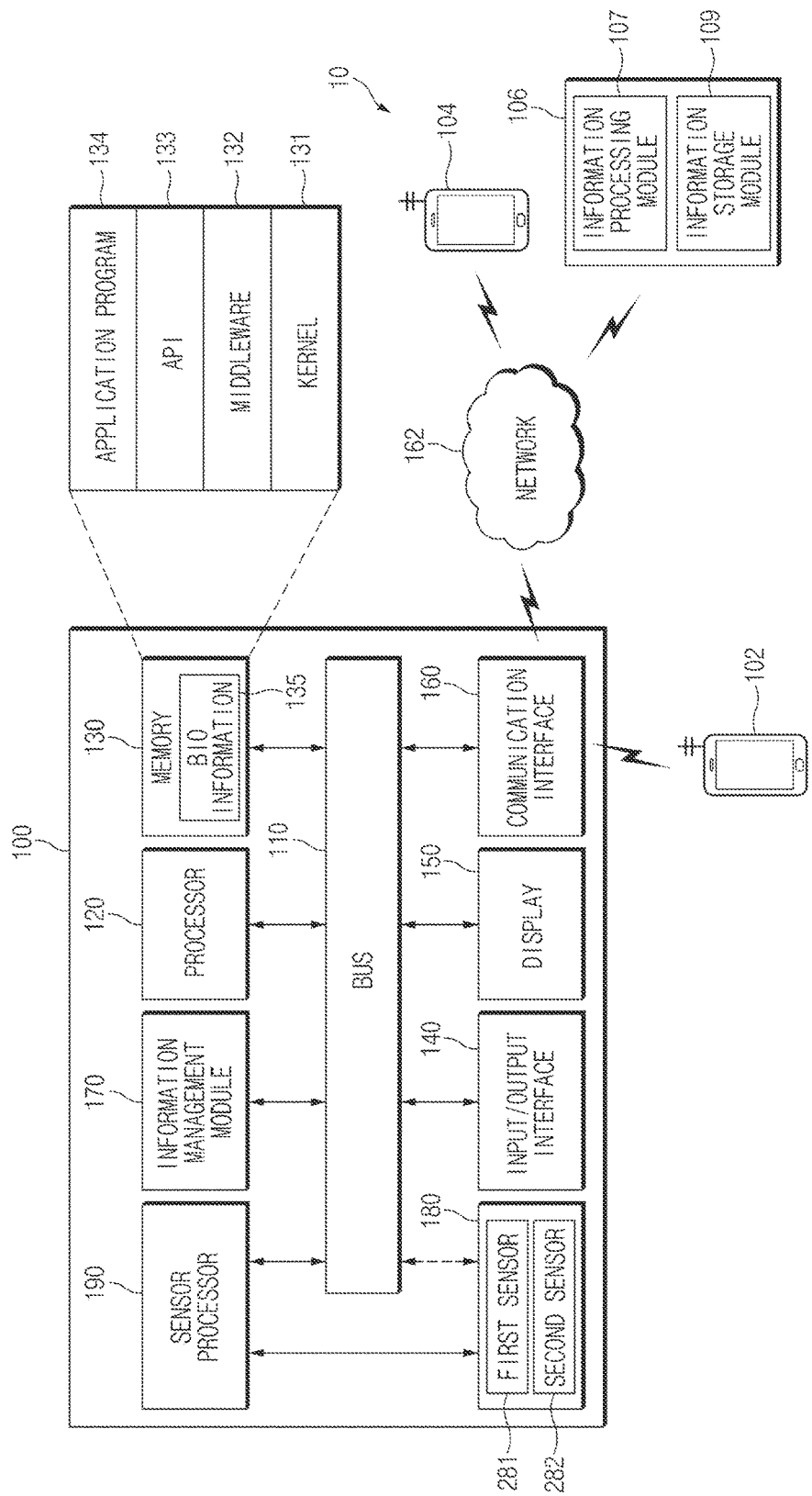
FIG. 2 is a view illustrating an electronic device information management system performing image management according to various embodiments of the present disclosure.

FIG. 2 is a view illustrating an electronic device information management system performing image management according to various embodiments of the present disclosure.

Referring to FIG. 2, according to an embodiment, an information management system 10 may include an electronic device 100, external electronic devices 102 and 104, a server device 106, and a network 162.

In the above-mentioned information management system 10, the network 162 may support a communication channel establishment between the electronic device 100 and the electronic device 104. The network 162, for example, may include network device components relating to a mobile communication channel establishment. Alternatively, the network 162 may include network device components relating to an internet communication channel establishment. The network 162 may support data transmission/reception between the electronic device 100 and the electronic device 104. Additionally, the network 162 may support data transmission/reception between the electronic device 100 and the server device 106. According to an embodiment, the network 162 may deliver bio information collected by the electronic device 100 to the server device 106. Alternatively, the network 162 may deliver bio information collected by the electronic device 100 to the electronic device 104.

The server device 106 may establish a communication channel with the electronic device 100 or the electronic device 104. According to an embodiment, the server device 106 may provide data relating to a specific application management of the electronic device 100. For example, the server device 106 may provide bio information related data (e.g., dosing information according to bio information, information on a bio state according to bio information, treatment information according to bio information, and health management information (e.g., diet information and exercise schedule information) according to bio information) to the electronic device 100 or the external electronic device 104.

According to various embodiments, the server device 106 may include an information processing module 107 and an information storage module 109 in order for bio information related service support. The information processing module 107 may establish a communication channel in correspondence to a communication connection request of the electronic device 100. The information processing module 107 may store bio information provided by the electronic device 100 in the information storage module 109. The information processing module 107 may transmit bio information based specific information, for example, at least one of bio related information and health management information, to the electronic device 100 according to a provided service format.

The information storage module 109 may store bio information provided by the electronic device 100. During this operation, the information storage module 109 may store bio information together with index information of the electronic device 100. The index information may include phone number information of the electronic device 100, user name or nickname information of the electronic device 100, specific character information that a user registers, and hardware identification information (e.g., MAC address information and serial information) of the electronic device 100. The information storage module 109 may accumulate bio information by each time and store the bio information. The information storage module 109 may provide the accumulated bio information in a list or graph form. When the bio information is managed by each phone number, although a user's electronic device has changed, if a phone number is maintained, the server device 106 may provide continuous bio information related service.

The server device 106 may support a registration operation in relation to the bio information store of the electronic device 100. For example, the server device 106 may provide to the electronic device 100 a server page (or a webpage) for inputting user information necessary for registration. When user information is collected from the electronic device 100, the server device 106 may register corresponding information. The server device 106 may store information (e.g., the user information) provided by the electronic device 100 in the information storage module 109. The server device 106 may provide specific bio information related service (e.g., service that provides health related useful information specified according to the current bio state or accumulated bio information) on the basis of bio information stored in the information storage module 109.

The external electronic device 102 may establish a communication channel with a communication interface 160 of the electronic device 100. For example, the external electronic device 102 may establish a short range communication channel or a wired communication channel with the communication interface 160. According to an embodiment, the external electronic device 102 may establish a Bluetooth communication channel or a WiFi direct communication channel with the communication interface 160. The external electronic device 104 may establish a communication channel with the electronic device 100 through the network 162. For example, the electronic device 104 may include a cellular communication module and may establish a communication channel with the electronic device 100. Alternatively, the electronic device 104 may include a WiFi communication module (not shown) and may establish a WiFi communication channel with the electronic device 100.

According to various embodiments, the external electronic device 102 or 104 may receive specific bio information from the electronic device 100. For example, the external electronic device 102 or 104 may receive bio information measured by the electronic device 100 in correspondence to a user control. According to an embodiment, a user of the external electronic device 102 or 104 may measure bio information by using the electronic device 100 and may manage the electronic device 100 to transmit the measured bio information to the external electronic device 102 or 104. The external electronic device 102 or 104 may accumulate and store bio information received from the electronic device 100 on the basis of time and index information. The external electronic device 102 or 104 may provide the stored bio information to the server device 106. The external electronic device 102 or 104 may receive bio information related service information from the server device 106 to store or output the bio information.

The electronic device 100 may include a sensor module 180 relating to bio information collection. The electronic device 100 may activate the sensor module 180 in correspondence to a specified trigger signal occurrence. The electronic device 100 may determine whether there is a user body contact (or an approach within a specified distance with the sensor module 180) by using the activated sensor module 180 and may process at least one of output, store, and transmission by detecting bio information when a user body contacts the sensor module 180. During bio information transmission, the electronic device 100 may establish a communication channel with at least one of the external electronic devices 102 and 104 and the server device 106.

The electronic device 100 may include a bus 110, a processor 120, a memory 130, an input/output interface 140, a display 150, a communication interface 160, an information management module 170, and a sensor module 180. Additionally, or alternatively, the electronic device 100 may further include a sensor processor 190.

The bus 110 may be a circuit connecting the above-mentioned components and performing a communication (e.g., delivering a control message, an input event, and data) between the above-mentioned components. For example, the bus 110 may deliver an input signal inputted from the input/output interface 140 to at least one of the processor 120 and the information management module 170. Additionally, the bus 110 may deliver a control signal of the processor 120 or the information management module 170 to the memory 130. According to an embodiment, the bus 110 may deliver a trigger signal relating to the activation of the sensor module 180 to the information management module 170 (or the processor 120, or the sensor processor 190). The bus 110 may deliver a sensor signal collected by the sensor module 180 to the information management module 170. The bus 110 may deliver bio information to the memory 130 or the communication interface 160 in correspondence to a control of the information management module 170. The bus 110 may deliver the collected bio information to the display 150.

The processor 120, for example, may receive instructions from the above-mentioned other components (e.g., the memory 130, the input/output interface 140, the display 150, the communication interface 160, the sensor processor 190, or the information management module 170) through the bus 110. The processor 120 may interpret the received instructions and may execute calculation or data processing according to the interpreted instructions. The processor 120 may be prepared in a form including at least one of the information management module 170 and the sensor processor 190, or in a form separated from the information management module 170 and the sensor processor 190, or in a form for controlling the memory 130 and the display 150 on the basis of the bus 110 or directly. The processor 120 may support a trigger signal collection state control (e.g., a control for an activation or deactivation of the touch sensor 181 and an activation or deactivation of the sensor module 180), a user body contact check, bio information collection, information output relating to collected bio information, transmission of bio information, and bio information related service information reception processing.

The memory 130 may store instructions or data received from the processor 120 or the other components (e.g., the input/output interface 140, the display 150, the communication interface 160, the sensor processor 190, or the information management module 170) or generated by the processor 120 or the other components. The memory 130, for example, may include programming modules such as a kernel 131, a middleware 132, an application programming interface (API) 133, or an application 134. Each of the above-mentioned programming modules may be configured with software, firmware, hardware, or a combination of at least two thereof.

The kernel 131 may control or manage system resources (e.g., the bus 110, the processor 120, the memory 130, the storage 180, and information management module 170) used for performing operations or functions implemented in the remaining other programming modules, for example, the middleware 132, the API 133, or the application 134. Additionally, the kernel 131 may provide an interface for performing a controlling or managing operation by accessing an individual component of the electronic device 100 from the middleware 132, the API 133, or the application program 134.

The middleware 132 may serve as an intermediary role for exchanging data as the API 133 or the application 134 communicates with the kernel 131. Additionally, in relation to job requests received from the application 134, the middleware 132, for example, may control (e.g., scheduling or load balancing) for the job requests by using a method of assigning a priority for using a system resource (e.g., the bus 110, the processor 120, the memory 130, the information management module 170, or the sensor processor 190) of the electronic device 100 to at least one application among the applications 134.

The API 133 may be an interface for allowing the application 134 to control a function provided from the kernel 131 or the middleware 132. The API 133, for example, may include at least one interface or function (e.g., an instruction) for file control, window control, image processing, or character control.

According to various embodiments, the application 134 may include SMS/MMS applications, e-mail applications, calendar applications, notification applications, health care applications (e.g., applications for measuring exercise amount or blood glucose), or environmental information applications (e.g., applications for providing pressure, humidity, or temperature information). Additionally or alternatively, the application 134 may be an application relating to information exchange between the electronic device 100 and an external electronic device (e.g., the electronic device 102 or 104). The information exchange related application, for example, may include a notification relay application for relaying specific information to the external device or a device management application for managing the external electronic device.

For example, the notification relay application may have a function for relaying to an external electronic device (e.g., the external electronic device 102 or 104) notification information occurring from another application (e.g., an SMS/MMS application, an e-mail application, a health care application, or an environmental information providing application) of the electronic device 100. Additionally or alternatively, the notification relay application may receive notification information from an external electronic device (e.g., the external electronic device 102 or 104) notification and may then provide the received notification information to a user. The device management application, for example, may manage (e.g., install, delete, or update) at least part of function (turn-on/turn off of the external electronic device (or some components thereof) or the brightness (or resolution) adjustment of a display) of an external electronic device (e.g., the external electronic device 102 or 104) communicating with the electronic device 100, an application operating in the external electronic device, or a service (e.g., call service or message service) provided from the external device. According to various embodiments, when an external electronic device is an MP3 player, the application 134 may include an application relating to music playback. Similarly, when an external electronic device is a mobile medical device, the application 134 may include an application relating to heath care.

According to an embodiment, the application 134 may support a bio information related function. For example, the application 134 may collect bio information 135 in correspondence to a trigger signal occurrence and may provide a function for outputting the collected bio information 135 to the display 150. The application 134 may provide a function for transmitting the collected bio information to an external electronic device (e.g., the external electronic device 102 or 104) or the server device 106. The application 134 may provide a function for receiving bio information related service information from the server device 106 and storing or outputting the bio information. The application 134 may provide a function for adjusting the setting of at least one of the touch sensor 181 and the sensor module 180 relating to trigger signal collection and a function for determining whether a user body contacts on the basis of the sensor module 180.

According to various embodiments, the application 134 may be prepared in an integration application. For example, the application 134 may include a first program module for supporting a bio information collection and output function and a second program module for supporting the storage and transmission of the collected bio information 135 and the reception and processing of service information relating to bio information. The first program module may be disposed in the memory 130 to support a bio information collection and output function in relation to bio information collection. The second program module may be disposed in the memory 130 when a request relating to the storage and transmission of the bio information 135 occurs while the first program module operates. When a bio information 135 store or transmission related function is completed or terminated, a second program module based function may be terminated. After a second program module based function termination, memory returning may be performed.

According to various embodiments, a trigger signal processing related first sub program module in the first program module may be disposed in the memory 130 and managed. When a specified trigger signal is collected, at least one of a second sub program module relating to whether a user body contacts, a third sub program module relating to bio information collection, and a fourth sub program module relating to a bio information output in the first program module may be disposed in the memory 130 and managed. According to various embodiments, the trigger signal processing related first sub program module may be embedded in the sensor processor 190 (e.g., a sensor hub).

The input/output interface 140 may deliver an instruction or data inputted from a user through an input/output device (e.g., a sensor, a keyboard, or a touch screen) to the processor 120, the memory 130, the communication interface 160, the information management module 170, or the sensor processor 190 through the bus 110. Additionally, the input/output interface 140, for example, may output through the input/output device (e.g., a speaker or a display) instructions or data received from the processor 120, the memory 130, the communication interface 160, the information management module 170, or the sensor processor 190 through the bus 110. According to various embodiments, the input/output interface 140 may include a physical key button (e.g., a home key, a side key, and a power key), a jog key, and a keypad. The input/output interface 140 may include a virtual keypad outputted to the display 150 as an input device. The input/output interface 140 may generate an input signal relating to at last one application execution or an input signal for requesting the power supply for the turned-off electronic device 100.

According to various embodiments, the input/output interface 140 may generate an input signal relating to the activation or deactivation of the touch sensor 181. Alternatively, at least some buttons in the input/output interface 140 may be disposed in an area adjacent to the sensor module 180 instead of the touch sensor 181. According to various embodiments, the input/output interface 140 may generate an input event for requesting the store of the collected bio information 135 or an input event for requesting the transmission of bio information in correspondence to a user control.

According to various embodiments, the input/output interface 140 may perform a function relating to audio processing. In relation to this, the input/output interface 140 may include one or more of at least one of a speaker and a microphone. The input/output interface 140, for example, may output audio data relating to a specific application execution through a speaker according to a control of the information management module 170.

The display 150 may display various information (e.g., multimedia data or text data). For example, the display 150 may output a lock screen and a standby screen. The display 150 may output a specific function execution screen, for example, a music playback screen, a video playback screen, and a broadcast reception screen, in correspondence to a function execution. According to an embodiment, the display may output a screen relating to a data processing method of application. For example, the display 150 may have a turned-off screen in a sleep state (e.g., a state in which power is cut off in the display 150 and a state in which the processing amount of the processor 120 in the electronic device 100 is limited to less than a predetermined value) of the electronic device 100. The display 150 may output at least one of a predetermined image and text specified in correspondence to a trigger signal occurrence in a turned-off screen state. According to various embodiments, when a lock is set, the display 150 may output a lock-screen. The display 150 may output at least one of an image and text relating to bio information collection on a lock-screen. According to various embodiments, when a lock is released, the display 150 may output a lock release screen (e.g., a standby screen, a home screen, a given specific function screen, and an execution screen of an execution requested function). The display 150 may output at least one of a bio information related image and text specified in correspondence to a screen being outputted in a lock released state.

The communication interface 160 may connect a communication between the electronic device 100 and an external device (e.g., at least one of the electronic device 102 or 104 and the server device 106). For example, the communication interface 160 may communicate with the external device in connection to the network 162 through wireless communication or wired communication. The wireless communication, for example, may include at least one of WiFi, Bluetooth (BT), near field communication (NFC), global positioning system (GPS), and cellular communication (e.g., LTE, LTE-A, CDMA, WCDMA, UMTS, WiBro, or GSM). The wired communication may include at least one of universal serial bus (USB), high definition multimedia interface (HDMI), recommended standard 232 (RS-232), and plain old telephone service (POTS), for example.

According to an embodiment, the network 162 may be telecommunications network. The telecommunications network may include at least one of computer network, internet, internet of things, and telephone network. According to an embodiment of the present disclosure, a protocol (e.g., transport layer protocol, data link layer protocol, or physical layer protocol) for communication between the electronic device 100 and an external device may be supported by at least one of the application 134, the application programming interface 133, the middleware 132, the kernel 131, and the communication interface 160.

The communication interface 160 may include a plurality of communication modules when the electronic device 100 supports a plurality of communication methods. For example, the electronic device 100 may include a communication module, for example, a short range communication module or a direct communication module, capable of establishing a direct communication channel with the electronic device 102. The short range communication module or the direct communication module may include at least one of various communication modules such as a WiFi direct communication module, a Bluetooth communication module, and a Zigbee communication module. Alternatively, the direct communication module may include a wired communication module such as cable.

According to an embodiment, the communication interface 160 may transmit bio information to at least one of the electronic device 102 or 104 and the server device 106. Additionally, the communication interface 160 may receive bio information related service information from at least one of the electronic device 104 and the server device 106. Service information received through the communication interface 160 may be stored in the memory 130 or outputted to the display 150.

The sensor processor 190 may be connected to the information management module 170 or the processor 120 through the bus 110. The sensor processor 190 may be directly connected to the sensor module 180. The sensor processor 190 may support at least part of a function management in the management of the sensor module 180 in correspondence to setting. For example, the sensor processor 190 may determine whether a trigger signal occurs by controlling a management of the touch sensor 181 included in the sensor module 180. The sensor processor 190 may determine whether a trigger signal occurs by controlling the light emitting unit 182 included in the sensor module 180. During this operation, the sensor processor 190, as described above, may adjust an activation or deactivation period of the touch sensor 181 or the sensor module 180. When a trigger signal occurs, the sensor processor 190 may deliver a corresponding trigger signal to the information management module 170. According to various embodiments, an operation relating to a trigger signal management of the sensor processor 190 may be processed in the information management module 170. Correspondingly, the sensor processor 190 may be omitted from the electronic device 100.

The sensor module 180 may include at least one of a first sensor 281 and a second sensor 282. The first sensor 281 may be used to detect a trigger signal of the touch sensor 181. The second sensor 282 may be used to determine whether a user's body part contacts or collect bio information. For example, the second sensor 282 may be a heart rate measurement sensor. According to various embodiments, the sensor module 180 may have a structure including only the second sensor 282 without the first sensor 281 relating to a trigger signal detection.

The information management module 170 may process data obtained from other components (e.g., the processor 120, the memory 130, the input/output interface 140, or the communication interface 160). For example, the information management module 170 may process at least one of trigger signal collection, confirmation on whether a user body contacts, bio information collection, the store of the bio information 135, and the transmission of the bio information 135.

Figure 3:
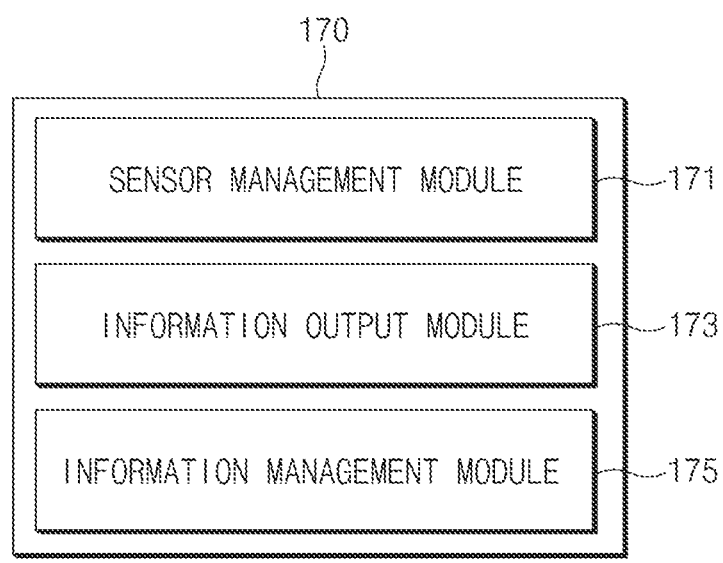
FIG. 3 is a view illustrating an information management module according to various embodiments of the present disclosure.

FIG. 3 is a view illustrating an information management module according to various embodiments of the present disclosure.

Referring to FIG. 3, an information management module 170 may include a sensor management module 171, an information output module 173, and an information management module 175.

The sensor management module 171 may control a sensor module 180 management of the electronic device 100. The sensor management module 171, for example, may be disposed in the information management module 170 or the sensor processor 190 to control a sensor module 180 management. According to an embodiment, in relation to the sensor module 180 including the first sensor 281 and the second sensor 282, the sensor management module 171 may detect whether there is an object contact (or approach) by activating the first sensor 281. In relation to this, the sensor management module 171 may control a power supply, activation period, or deactivation period relating to the management of the first sensor 281. For example, the sensor management module 171 may maintain the first sensor 281 to be in a turn-on state (or an activation state) while power is supplied to the electronic device 100. Alternatively, the sensor management module 171 may activate or deactivate the first sensor 281 at a predetermined period.

The sensor management module 171 may activate the second sensor 282 when an object contact is detected during an activation period of the first sensor 281. The sensor management module 171 may determine whether there is a user body contact by activating the second sensor 282. For example, the sensor management module 171 may determine whether a sensor signal collected by the second sensor 282 is a given specific sensor signal (e.g., a sensor signal occurring when a user body contacts). When there is no user body part contact, the sensor management module 171 may deactivate the second sensor module 282. When the second sensor 282 is deactivated, the sensor management module 171 may determine whether there is an object contact by activating the first sensor 281. According to an embodiment, when a sensor signal is received from the second sensor 282 more than a predetermined number of times (e.g., an object contacts continuously) within a predetermined time, the sensor management module 171 determines that there is no user body contact. In this case, the sensor management module 171 may adjust (e.g., adjust a deactivation time to be longer) a deactivation period of the first sensor 281. When it is determined that there is a user body contact on the basis of a sensor signal collected by the second sensor 282, the sensor management module 171 may control a bio information collection on the basis of the second sensor 282. When bio information is collected on the basis of the second sensor 282, the sensor management module 171 may provide the collected bio information to the information output module 173.

According to various embodiments, in the case that the sensor module 180 including only the second sensor 282 is managed, the sensor management module 171 may control an activation or deactivation of the second sensor 282 at a predetermined period. Alternatively, the sensor management module 171 may maintain the second sensor 282 to be in a turn-on state while power is supplied to the electronic device 100. When a sensor signal collected by the second sensor 282 has a signal value (e.g., a light amount change value according to an object contact or approach) according to an object approach, the sensor management module 171 may determine whether there is a user body part contact on the basis of the second sensor 282. When a sensor signal value provided from the second sensor 282 is a signal value corresponding to a user body part contact, the sensor management module 171 may control a bio information collection on the basis of the second sensor 282. The sensor management module 171 may provide the bio information collected by the second sensor 282 to the information output module 173. During the above-mentioned operation, the sensor management module 171 may perform a first operation control relating to whether there is an object contact, a second operation control relating to whether there is a user body contact, and a third operation control relating to a bio information collection. During this operation, the sensor management module 171 may adjust the light emission amount of the second sensor 282 by each operation control or adjust (e.g., adjust the sensitivity of an object check to be smaller than the sensitivity of a body check or adjust a body check sensitivity to be smaller than a bio information collection sensitivity) the sensitivity of the second sensor 282. The sensitivity relates to a sensing degree of a sensor and when the sensitivity is large, may provide a relatively high accuracy. According to various embodiments, the sensor management module 171 may determine whether a sensor signal obtained when an object contacts during a second sensor 282 management process is a signal value corresponding to a user body part contact. When a signal value corresponding to a user body contact is detected, the sensor management module 171 may control a second sensor 282 management relating to a bio information collection.

According to various embodiments, the sensor management module 171 may control at least one of the activation of the first sensor 281, the activation of the second sensor 282, a bio information collection, a bio information output, and a bio information output state change according to a state of the electronic device 100. For example, the sensor management module 171 may detect whether there is an object contact by activating the first sensor 281 or the second sensor 282 in a sleep state. The sensor management module 171 may determine whether to activate the first sensor 281 or the second sensor 282 in correspondence to the type of an application being executed in a lock state or a lock release state. For example, the sensor management module 171 may deactivate the first sensor 281 or the second sensor 282 while a call function is executed in a lock setting state or a lock release state. When a specific event (e.g., a function selection event relating to the management of the sensor module 180) occurs during a call function execution, the sensor management module 171 may activate the first sensor 281 or the second sensor 282. According to an embodiment, the sensor management module 171 may deactivate the first sensor 281 or the second sensor 282 while a video function is executed.

When bio information is received from the sensor management module 171, the information output module 173 may output the received bio information. In relation to this, the information output module 173 may output at least one of an image and text relating to bio information on the display 150 of the electronic device 100. According to an embodiment, when bio information collection occurs in a sleep state, the information output module 173 may output a layer including a bio information related image or text to an entire area of the display 150. When bio information collection occurs in a lock-screen state, the information output module 173 may output a bio information related image or text to a predetermined area of the display 150. When bio information collection occurs in a lock-release state, the information output module 173 may output a bio information related image or text on the basis of a bio information related application screen. Alternatively, when bio information collection occurs in a lock-release state, the information output module 173 may obtain a predetermined area by adjusting a screen on the display 150. The information output module 173 may output a bio information related image or text to the obtained area. As mentioned above, the information output module 173 may adjust at least one of the size, content, and format of bio information related information to be outputted according to a sleep state, a lock screen state, and a lock release state. The information output module 173 may output bio information related information of which at least one of the size, content, and format is adjusted.

According to various embodiments, during bio information output, the information output module 173 may output a menu item or icon relating to at least one function selection of storage and transmission. Alternatively, the information output module 173 may allocate a bio information store or transmission related function execution to a specific hardware key. When an event for requesting a bio information store occurs, the information output module 173 may store the bio information in the memory 130 temporarily or semi-permanently. According to an embodiment, the information output module 173 may output an input window for inputting stored user information in relation to the bio information store. Alternatively, when there is a bio information store request, the information output module 173 may output an input window relating to a set security information input. Alternatively, the information output module 173 may store bio information on the basis of index information of the electronic device 100.

According to various embodiments, when a request relating to bio information transmission occurs, the information output module 173 may transmit the bio information to the server device 106. Alternatively, the information output module 173 may output an interface relating to the phone number of the other electronic device 102 or 104 or an address information input of the server device 106, where the bio information is to be transmitted. When a corresponding phone number or address information is inputted, the information output module 173 may transmit the bio information to at least one of the other electronic devices 102 and 104 and the server device 106. When service information relating to the transmitted bio information is received from the server device 106, the information output module 173 may store the service information in the memory 130 or output the transmitted bio information to the display 150.

The information management module 175 may support the management of the stored bio information. The information management module 175 may generate a list of bio information stored in the memory 130. The information management module 175 may generate a time graph on the basis of bio information. When service information corresponding to a bio information value is stored, the information management module 175 may output corresponding service information to the display 150.

According to various embodiments, the information management module 175 may accumulate and store user specified bio information. The information management module 175 may generate a user specific list or graph on the basis of the accumulated and stored user specific bio information. When bio information update occurs, the information management module 175 may output a list or graph of an updated bio information related user to the display 150. Alternatively, the information management module 175 may output to the display 150 a screen for determining entire stored bio information by each user and time in correspondence to an input event.

According to various embodiments, when specific bio information is a specified value (e.g., when a heart rate is more than a specified number), the information management module 175 may automatically transmit corresponding bio information to the server device 106. The information management module 175 may store the service information received from the service device 106 in relation to the transmitted bio information or output the service information to the display 150.

As mentioned above, according to various embodiments, an electronic device may include an information management module for activating a sensor to collect bio information on a contacted object when a trigger signal relating to the sensor activation for supporting bio information collection is detected, and a display for outputting the collected bio information.

According to various embodiments, the information management module may determine whether a contacted object is a user body according to the trigger signal detection and collect the bio information when the object is a user body.

According to various embodiments, the information management module may control the sensor activation according to at least one of a specified touch signal occurrence detection from a touch sensor disposed an area adjacent to the sensor, a specified pressure signal occurrence detection from a pressure sensor disposed in an area adjacent to the sensor, a contact point connection detection by a button disposed in an area adjacent to the sensor, and a specified proximity signal occurrence detection from a proximity sensor disposed in an area adjacent to the sensor.

According to various embodiments, the information management module may activate the sensor when a movement change of the electronic device where the sensor is disposed changes into a specified movement.

According to various embodiments, the information management module may activate the sensor when a direction of the front or rear of the electronic device rotates a predetermined number of times in a specified predetermined direction.

According to various embodiments, the information management module may activate the sensor at a predetermined period and may determine whether a sensor signal corresponding to an object approach to the sensor is detected during the activation period.

According to various embodiments, when the trigger signal is detected, the information management module may activate the sensor or maintain a deactivation state according to a display turn-on state of the electronic device and the type of an application being executed in the electronic device.

According to various embodiments, the information management module may store or transmit the bio information in correspondence to an input event relating to at least one of the storage and transmission of the bio information.

According to various embodiments, the information management module may output to the display at least one of a security information input window and a lock setting screen when the input event is received.

According to various embodiments, the information management module may store the bio information in a memory or transmit the bio information to a specified device when specified security information or specified lock release information is inputted.

Figure 4:
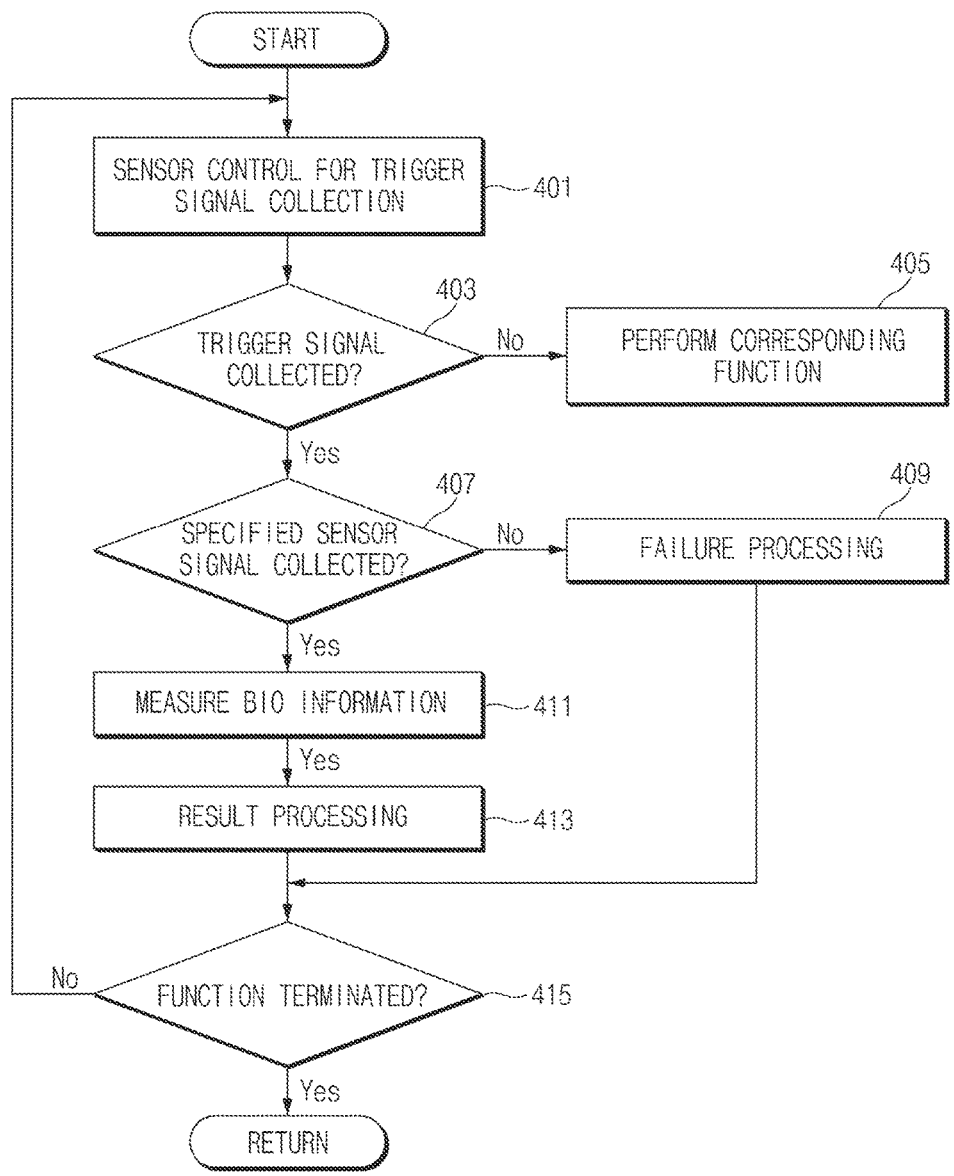
FIG. 4 is a view illustrating an information management method according to various embodiments of the present disclosure.

FIG. 4 is a view illustrating an information management method according to various embodiments of the present disclosure.

Referring to FIG. 4, in relation to an information management method according to various embodiments, the information management module 170 may perform a sensor control for trigger signal collection in operation 401. For example, the information management module 170 may activate at least one of the first sensor 281 and the second sensor 282.

In operation 403, the information management module 170 may determine whether a specified trigger signal is collected. For example, the information management module 170 may determine whether sensor signal collected by the activated first sensor 281 (e.g., a touch sensor, a barometric pressure sensor, and a button) is a signal value corresponding to an object contact or approach detection. Alternatively, the information management module 170 may determine whether a sensor signal provided from the second sensor 282 activated at a predetermined period is a signal value corresponding to an object contact or approach detection.

When a specified trigger signal is not collected in operation 403, the information management module 170 may control a corresponding function performance in operation 405. In relation to a corresponding function performance, the information management module 170 may maintain a previous state (e.g., a sleep state, a lock state, and a specific function execution state) of the electronic device 100. Alternatively, when a specific input event occurs, the information management module 170 may support function processing in correspondence to a corresponding event, for example, a file playback function, a web access function, and a stored bio information search function in correspondence to input event type.

When a specified trigger signal is collected in operation 403, the information management module 170 may determine whether a specified sensor signal is collected in operation 407. In relation to this, when the specified trigger signal is collected, the information management module 170 may activate the second sensor 282. The sensor management module 170 may determine whether a sensor signal value according to a user body (e.g., finger) contact is collected by using the activated second sensor 282. During this operation, the sensor management module 170 may activate the second sensor 282 for a specified time and determine whether a specified sensor signal is collected for a corresponding time (that is, the specified time).

When the specified sensor signal is not collected in operation 407, the information management module 170 may perform failure processing in operation 409, for example. According to an embodiment, when a specified sensor signal is not collected for a specified time, the information management module 170 may deactivate the second sensor 282. According to an embodiment, the information management module 170 may output a notification (e.g., at least one of audio information and video information) when a specified sensor signal is not collected, through at least one of the input/output interface 140 and the display 150. Alternatively, the information management module 170 may control the activation of the first sensor 281 without an additional notification output. After performing the failure processing, the information management module 170 branches into operation 401 through operation 415 to activate the first sensor 281 in relation to trigger signal collection or manage the second sensor 282 to collect trigger signals.

In operation 407, when a specified sensor signal is collected (e.g. a signal corresponding to a user body contact is received), the information management module 170 may perform a bio information measurement in operation 411. In relation to this, the information management module 170 may manage the second sensor 282 relating to the bio information measurement. The information management module 170 may process the initialization and light emission and reception of the second sensor 282 relating to the specified sensor signal collection or the initialization and light emission and reception of the second sensor 282 relating to the bio information measurement.

According to various embodiments, the information management module 170 may omit the operation for determining whether the second sensor 282 based specified sensor signal is collected in operation 407. In this case, when a trigger signal is collected in operation 403, the information management module 170 may control a second sensor management relating to a bio information measurement operation in operation 411.

In operation 413, the information management module 170 may control result processing relating to bio information measurement. For example, the information management module 170 may support at least one of the output, store, and transmission of the measured bio information.

In operation 415, the information management module 170 may determine whether there is a bio information measurement related function termination event (e.g., a predetermined time elapse after bio information measurement and the occurrence of an input event indicating bio information measurement termination). When there is no function termination event occurrence in operation 415, the information management module 170 may branch into operation 401 to perform the subsequent processes again.

Figure 5:
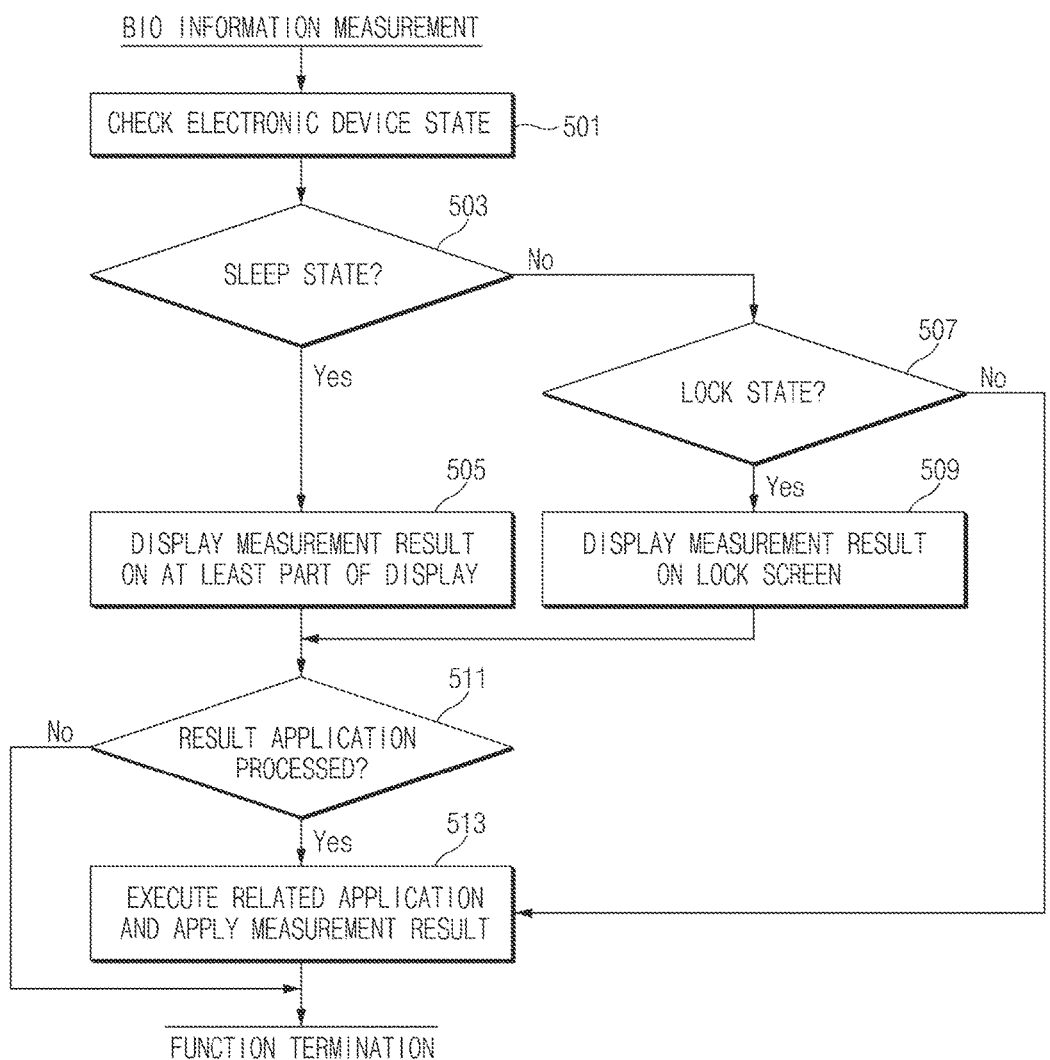
FIG. 5 is a view illustrating an information management method depending on an electronic device state according various embodiments of the present disclosure.

FIG. 5 is a view illustrating an information management method depending on an electronic device state according various embodiments of the present disclosure.

Referring to FIG. 5, in relation to an information management method depending on an electronic device state, when bio information is measured, the information management module 170 may determine an electronic device 100 state value in operation 501. For example, in operation 503, the information management module 170 may determine whether the electronic device 100 is in a sleep state. When the electronic device 100 is in a sleep state in operation 503, the information management module 170 may display a measurement result on at least part of the display 150 in operation 505. In relation to this, the information management module 170 may supply power to the display 150 in a sleep state and output at least one of an image or text corresponding to a measurement result.

When the electronic device 100 is not in a sleep state in operation 503, the information management module 170 may determine whether the electronic device 100 is in a lock state (or a lock screen output state) in operation 507. When the electronic device 100 is in a lock state in operation 507, the information management module 170 may display a measurement result on a lock screen in operation 509. When the electronic device 100 is not in a lock state, for example, a lock release state, in operation 507, the information management module 170 may branch into operation 513. When a measurement result is displayed on a lock screen, the information management module 170 may dispose a layer including at least one of an image and text corresponding to the measurement result to be overlaid on a lock screen. Alternatively, the information management module 170 may reconfigure a lock screen in order to allow a measurement result to be displayed on a partial area of the display 150. According to various embodiments, the information management module 170 may output a measurement result as audio information.

After a measurement result is displayed in operation 505 or operation 509, the information management module 170 may determine whether an input event relating to result application processing is received in operation 511. In relation to this, the information management module 170 may output an icon or virtual key button relating to the store or transmission of bio information or may allocate a hardware key.

When an input event relating to result application processing is received in operation 511, the information management module 170 may process related application execution and measurement result application in operation 513. For example, the information management module 170 may automatically execute an application relating to bio information and output a measurement result to an application execution screen. Herein the information management module 170 may display currently measured bio information together with previously stored bio information. According to various embodiments, the information management module 170 may select a corresponding icon or virtual key button to receive a request relating to bio information store. When a store request is received, the information management module 170 may store bio information in the memory 130. According to an embodiment, the information management module 170 may perform a security information (e.g., password) verification procedure before bio information is stored. According to an embodiment, the information management module 170 may perform an input procedure on user information (e.g., name, nickname, and phone number). When user information is inputted, the information management module 170 may perform a security information verification procedure. When bio information transmission is requested, the information management module 170 may transmit bio information to a specified device or a special device corresponding to input information. On the basis of the above-mentioned operations, even if bio information is collected by using another user's electronic device, by transmitting, storing, and managing the bio information to a user's electronic device, various embodiments may support continuous bio information related data search and service management.

When there is no input event relating to result application processing in operation 511, the information management module 170 may skip operation 513. Alternatively, the information management module 170 may branch into operation 415 of FIG. 4 to determine whether a function is terminated.

As mentioned above, according to various embodiments, an information management method may include receiving a trigger signal relating to sensor activation for supporting bio information collection, collecting bio information on a contacted object by activating the sensor when the trigger signal is detected, and outputting the collected bio information.

According to various embodiments, the collecting of the bio information may include determining whether a contacted object is a user body according to the trigger signal detection and collecting the bio information when the object is a user body.

According to various embodiments, the receiving of the trigger signal includes at least one of receiving a specified touch signal occurrence from a touch sensor disposed an area adjacent to the sensor, receiving a specified pressure signal occurrence from a pressures sensor disposed in an area adjacent to the sensor, receiving a contact point connection by a button disposed in an area adjacent to the sensor, and receiving a specified proximity signal occurrence from a proximity sensor disposed in an area adjacent to the sensor.

According to various embodiments, the receiving of the trigger signal includes detecting whether a movement change of an electronic device where the sensor is disposed is a specified movement change.

According to various embodiments, the receiving of the trigger signal may include detecting whether a direction of the front or rear of the electronic device is rotated and changed a predetermined number of times in a predetermined direction.

According to various embodiments, the receiving of the trigger signal may include activating the sensor at a predetermined period and determining whether a sensor signal corresponding to an object approach to the sensor is detected during the activation period.

According to various embodiments, the method further include, when the trigger signal is detected, determining a state of an electronic device, and performing a control to activate a sensor according to the trigger signal or maintain a deactivation state according to a display turn-on state of the electronic device or the type of an application being executed in the electronic device.

According to various embodiments, the method may further include receiving an input event relating to at least one of the storage and transmission of the bio information, and storing or transmitting the bio information in correspondence to the input event.

According to various embodiments, the method may further include outputting at least one of a security information input window and a lock setting screen when the input event is received.

According to various embodiments, the method may further include storing the bio information in a memory or transmit the bio information to a specified device when specified security information or specified lock release information is inputted.

Figure 6:
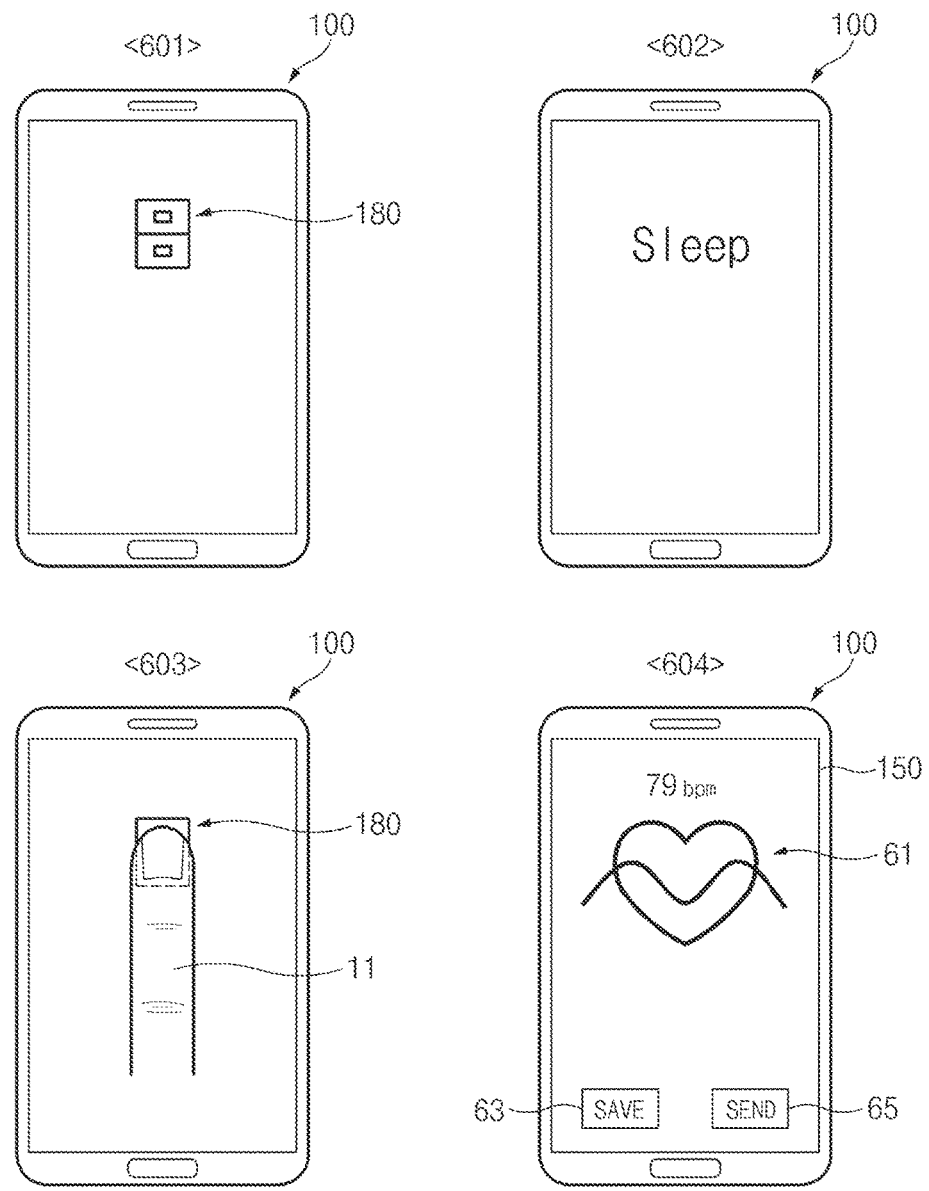
FIG. 6 is a view illustrating a screen interface relating to a sleep state based information management of an electronic device according various embodiments of the present disclosure.

FIG. 6 is a view illustrating a screen interface relating to a sleep state based information management of an electronic device according various embodiments of the present disclosure.

Referring to FIG. 6, as shown in a state 601, a sensor module 180 may be disposed at one side (e.g., the rear of the electronic device 100) of the electronic device 100. Additionally, as shown in a state 602, the electronic device 100 may be in a sleep state (e.g., a state in which the display 150 is turned off).

According to an embodiment, as shown in a state 603, when a user finger 11 contacts the sensor module 180, the information management module 170 may perform bio information collection. According to various embodiments, when the user finger 11 contacts the sensor module 180, the information management module 170 may determine an object contact on the basis of a sensor signal provided from the activated first sensor 281 or the second sensor 282 managed by trigger signal detection. When an object contacts, the information management module 170 may activate the second sensor 282. Alternatively, the information management module 170 may determine whether an object contact is a user finger 11 contact by using the activated second sensor 282. When a sensor signal corresponding to the user finger 11 contact is received from the second sensor 282, the information management module 170 may manage the second sensor 282 as bio information collection. In relation to the above-mentioned operation, a user may perform an operation for contacting the sensor module 180 three times. According to various embodiments, when the electronic device 100 is set or designed to omit a procedure for determining whether a user finger contacts, a user may perform an operation for allowing a finger to contact the sensor module 180 twice. According to various embodiments, the trigger signal may be a state change value of the electronic device 100 by an acceleration sensor or a geomagnetic sensor. For example, when an operation for overturning the front and rear of the electronic device 100 occurs for a predetermined number of times (e.g., an operation for allowing the rear to face a user once and an operation for allowing the front to face a user once), the information management module 170 may recognize this as a trigger signal. For example, when a user performs an operation for determining a sensor module disposed at the rear of the electronic device 100, the information management module 170 may activate the second sensor 282. Additionally, the information management module 170 may be set or designed to omit an operation for determining whether a user finger contacts. In this case, a user may perform an operation for allowing a finger to contact the sensor module 180 after an operation for overturning the electronic device 100. The information management module 170 may manage (e.g., activate) a bio information measurement function in correspondence to an overturning operation and a finger contact operation. The electronic device 100 may provide a setting function (e.g., a menu or setting screen) for inserting or deleting a user finger contact determining procedure into or from a bio information measurement procedure.

When bio information is collected, as shown in a state 604, the information management module 170 may output a bio information image 61 to the display 150 automatically or in correspondence to a user input. Additionally or alternatively, the bio information image 61 may be a text corresponding to a bio information value. The information management module 170 may output a virtual save button 63 relating to bio information store to one side of the display 150. Additionally, the information management module 170 may output a virtual send button 65 relating to bio information transmission to one side of the display 150. When the save button 63 or the send button 65 is selected, the information management module 170 may output a related screen to the display 150.

According to various embodiments, when the save button 63 or the send button 65 is selected, the information management module 170 may output a lock screen to the display 150. When lock is released, the information management module 170 may output to the display 150 a screen relating to the save button 63 or the send button 65. If there is no lock setting, the information management module 170 may output to the display 150 a screen corresponding to the selection of the save button 63 or the send button 65 without a lock screen output operation.

Figure 7:
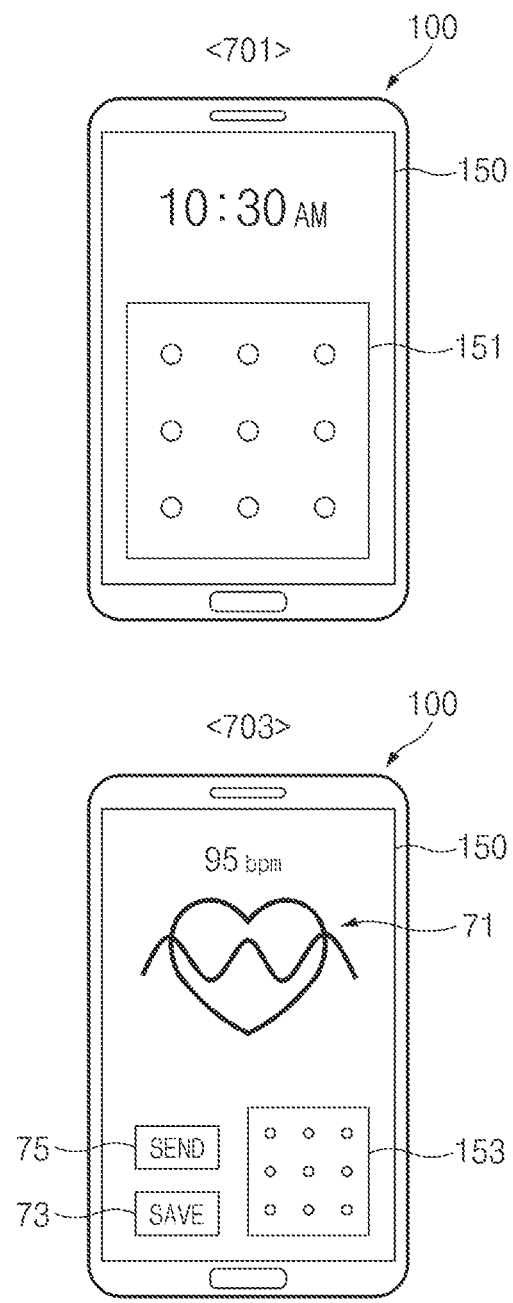
FIG. 7 is a view illustrating a screen interface relating to a lock state based information management of an electronic device according various embodiments of the present disclosure.

FIG. 7 is a view illustrating a screen interface relating to a sleep state based information management of an electronic device according various embodiments of the present disclosure.

Referring to FIG. 7, the electronic device 100 may output a lock screen to a display 150 as shown in a state 701. For example, when an event relating to a lock screen output occurs, or a wake-up event occurs in a sleep state, the electronic device 100 may output a lock screen to the display 150. According to an embodiment, the electronic device 100 may output a pattern lock image 151 in relation to the lock screen. According to various embodiments, the electronic device 100 may output a protection screen (e.g., a lock released screen in correspondence to a touch event occurrence) without an additional pattern lock to the display 150. Additionally, the electronic device 100 may output other information, for example, time information.

As shown in the state 603 of FIG. 6, when bio information is collected as a user finger contacts the sensor module 180, the information management module 170 may output a bio information image 71 as shown in a state 703. During this operation, the information management module 170 may output a change image obtained by changing at least one of the size, form, and content of the pattern lock image 151 to the display 150 in relation to a bio information image 71 output. According to various embodiments, the information management module 170 may adjust and output the form of the bio information image 71. For example, after reducing the size of a specified bio information image, the information management module 170 may output the size-reduced bio information image to one side of the display 150.

According to various embodiments, the information management module 170 may output to the display 150 at least one of a save button 73 relating to the store of bio information and a send button 75 relating to the transmission of bio information. When the save button 73 or the send button 75 is selected, the information management module 170 may output a lock release request related notification (e.g., a flash of a change image and a lock release requesting text). When lock is released, the information management module 170 may control a function corresponding to the selected button, for example, the store of bio information or the transmission of bio information. When the bio information is stored, the information management module 170 may store the bio information in the memory by default. During this operation, the information storage module 170 may match index information of the electronic device 100 and bio information to transmit the bio information. When lock is released after the send button 75 selection, the information management module 170 may automatically transmit bio information to the specified server device 106 or transmit bio information after performing a verification procedure.

Figure 8:
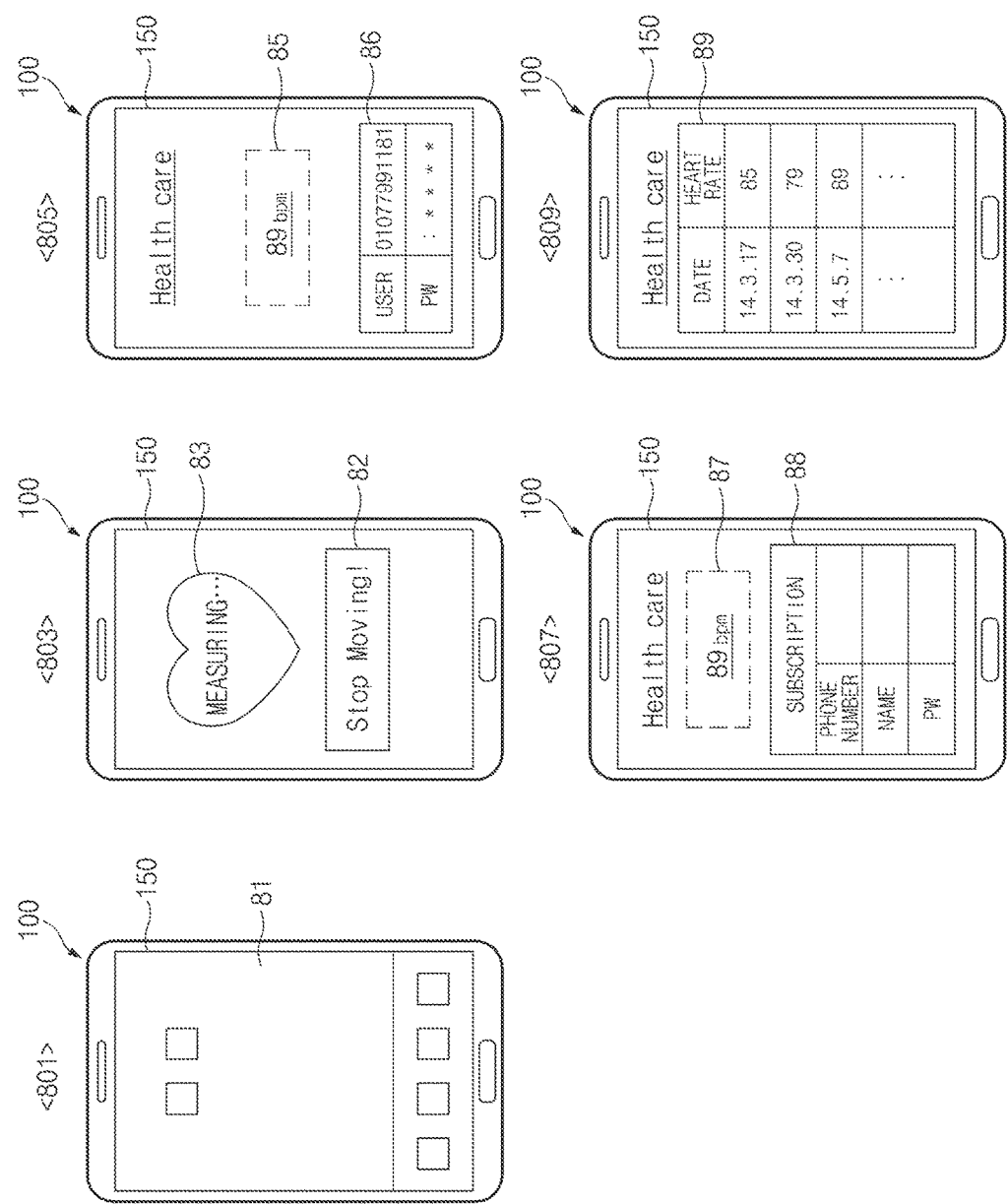
FIG. 8 is a view illustrating a screen interface relating to an information management of an electronic device according various embodiments of the present disclosure.

FIG. 8 is a view illustrating a screen interface relating to an information management of an electronic device according various embodiments of the present disclosure.

Referring to FIG. 8, as shown in a state 801, the electronic device 100 may output to, a predetermined area 81 of the display 150, a screen including at least one icon in states such as a lock release state, a standby screen, and a home screen. According to various embodiments, the electronic device 100 may output an execution screen according to a specific function execution to the predetermined area 81.

As shown in the state 603 of FIG. 6, when a user finger contacts the sensor module 180, the information management module 170 may collect bio information. Herein, as described above, the information management module 170 may perform a trigger signal detection relating to a bio information collection function management of the sensor module 180 and may collect bio information during trigger signal detection. The trigger signal detection operation may include a sensor signal reception operation specified by at least one of the first sensor 281 and the second sensor 282 included in the sensor module 180. The first sensor 281 may include a sensor for collecting a sensor signal according to a movement state of the electronic device 100, and a sensor for collecting a sensor signal by touch, pressure, or a button.

When an object recognized as a user finger contacts the sensor module 180, as shown in a state 803, the information management module 170 of the electronic device 100 may output information corresponding to a state to the display 150 during bio information measurement. For example, the information management module 170 may output to the display 150 a state image 83 representing a state during bio information measurement. The information management module 170 may output to the display 150 a state message 82 (e.g., guide information relating to bio information measurement) relating to a state during bio information measurement.

When bio information is collected, as shown in a state 805, the information management module 170 may output to the display 150 a screen relating to the collected bio information automatically or in correspondence to a bio information store request. For example, the information management module 170 may output bio information 85 to the display 150. Additionally, the information management module 170 may output an information input window 86 for inputting user information and security information relating to the bio information 85. When specified information (e.g., a phone number) is written in a user information input blank and specified information (e.g., a set password) is written in a security information input blank, the information management module 170 may store the collected bio information in the memory 130.

When bio information is collected, as shown in a state 807, the information management module 170 may output to the display 150 a screen relating to the collected bio information automatically or in correspondence to a bio information store request. For example, the information management module 170 may output bio information 87 to the display 150. The information management module 170 may receive a server page from the server device 106 in relation to the bio information 87 to output the received server page. When the electronic device 100 is not registered in the server device 106, the server device 106 may transmit a subscription information input window 88 relating to bio information related service subscription to the electronic device 100. As shown in the drawing, the information management module 170 may output the subscription information input window 88 to the display 150.

According to various embodiments, when the electronic device 100 is subscribed to bio information related service, the information management module 170 may transmit bio information to the server device 106. The information management module 170 may receive a bio accumulated information list 89 from the server device 106 so as to output the bio accumulated information list 89 to the display 150 as shown in a state 809. According to various embodiments, the bio accumulated information list 89 may be information generated by the information management module 170 on the basis of bio information stored in the memory 130.

As mentioned above, the information management module 170 may control a trigger signal occurrence detection relating to bio information collection. The information management module 170 may automatically activate a sensor for collecting bio information during trigger signal occurrence detection and also output a screen interface corresponding thereto automatically or in correspondence to a user input. Additionally, when bio information in a specified form (or a range recognized as human bio information) is collected, the information management module 170 may output at least one specified screen interface automatically or according to a user input.

Figure 9:
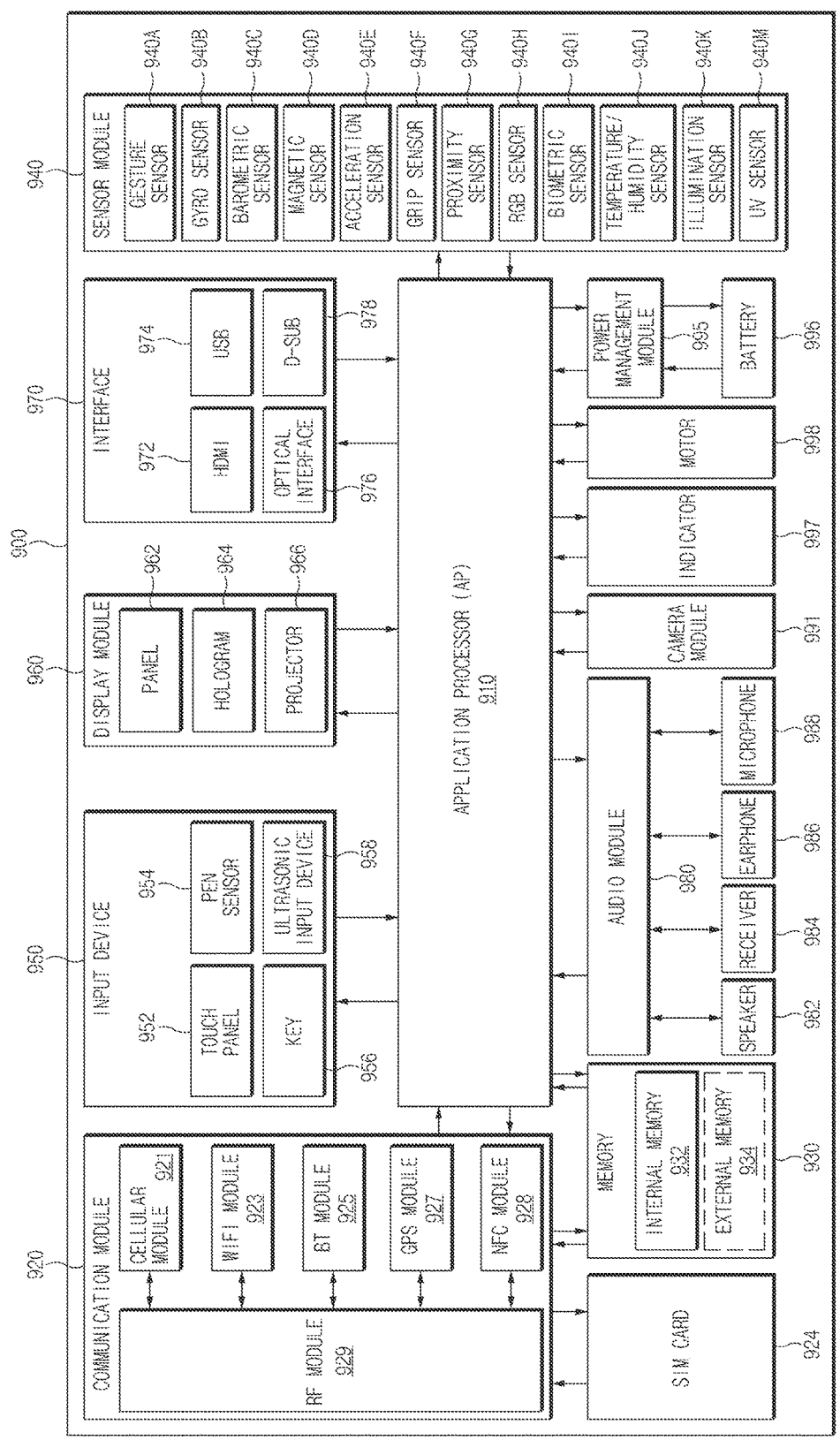
FIG. 9 is a block diagram illustrating an electronic device according to another embodiment of the present disclosure.

FIG. 9 is a block diagram illustrating an electronic device according to another embodiment of the present disclosure. The electronic device, for example, may configure all or part of the display 150 and the electronic device 100 shown in FIG. 2.

Referring to FIG. 9, an electronic device 900 may include at least one application processor (AP) 910, a communication module 920, a subscriber identification module (SIM) card 924, a memory 930, a sensor module 940, an input device 950, a display 960, an interface 970, an audio module 980, a camera module 991, a power management module 995, a battery 996, an indicator 997, and a motor 998.

The AP 910 may control a plurality of hardware or software components connected to the AP 910 and also may perform various data processing and operations with multimedia data by executing an operating system or an application program. The AP 910 may be implemented with a system on chip (SoC), for example. According to an embodiment of the present disclosure, the AP 910 may further include a graphic processing unit (GPU) (not shown).

The communication module 920 (e.g., the communication interface 160) may perform data transmission/reception through a communication between other electronic devices (e.g., the electronic device 102 or 104 or the server device 106) connected to the electronic device 900 (e.g., the electronic devices 100) via a network. According to an embodiment of the present disclosure, the communication module 920 may include a cellular module 921, a WiFi module 923, a BT module 925, a GPS module 927, an NFC module 928, and a radio frequency (RF) module 929.

The cellular module 921 may provide voice calls, video calls, text services, or internet services through a communication network (e.g., LTE, LTE-A, CDMA, WCDMA, UMTS, WiBro, or GSM). The cellular module 921 may perform a distinction and authentication operation on an electronic device in a communication network by using a subscriber identification module (e.g., the SIM card 924), for example. According to an embodiment, the cellular module 921 may perform at least part of a function that the AP 910 provides. For example, the cellular module 921 may perform at least part of a multimedia control function.

According to an embodiment of the present disclosure, the cellular module 921 may further include a communication processor (CP). Additionally, the cellular module 921 may be implemented with SoC, for example. As shown in FIG. 9, components such as the cellular module 921 (e.g., a CP), the memory 930, or the power management module 995 are separated from the AP 910, but according to an embodiment of the present disclosure, the AP 910 may be implemented including some of the above-mentioned components (e.g., the cellular module 921).

According to an embodiment of the present disclosure, the AP 910 or the cellular module 921 (e.g., a CP) may load instructions or data, which are received from a nonvolatile memory or at least one of other components connected thereto, into a volatile memory and then may process them. Furthermore, the AP 910 or the cellular module 921 may store data received from or generated by at least one of other components in a nonvolatile memory.

Each of the WiFi module 923, the BT module 925, the GPS module 927, and the NFC module 928 may include a processor for processing data transmitted/received through a corresponding module. Although the cellular module 921, the WiFi module 923, the BT module 925, the GPS module 927, and the NFC module 928 are shown as separate blocks in FIG. 9, according to an embodiment of the present disclosure, some (e.g., at least two) of the cellular module 921, the WiFi module 923, the BT module 925, the GPS module 927, and the NFC module 928 may be included in one integrated chip (IC) or an IC package. For example, at least some (e.g., a CP corresponding to the cellular module 921 and a WiFi processor corresponding to the WiFi module 923) of processors respectively corresponding to the cellular module 921, the WiFi module 923, the BT module 925, the GPS module 927, and the NFC module 928 may be implemented with one SoC.

The RF module 929 may be responsible for data transmission, for example, the transmission of an RF signal. Although not shown in the drawings, the RF module 929 may include a transceiver, a power amp module (PAM), a frequency filter, or a low noise amplifier (LNA). Additionally, the RF module 929 may further include components for transmitting/receiving electromagnetic waves on a free space in a wireless communication, for example, conductors or conducting wires. Although the cellular module 921, the WiFi module 923, the BT module 925, the GPS module 927, and the NFC module 928 share one RF module 929 shown in FIG. 9, according to an embodiment of the present disclosure, at least one of the cellular module 921, the WiFi module 923, the BT module 925, the GPS module 927, and the NFC module 928 may perform the transmission of an RF signal through an additional RF module.

According to various embodiments, the communication module 920 may transmit bio information of the electronic device 900 to at least one of the external electronic device 102 or 104 and the server device 106. The communication module 920 may receive bio information related service information transmitted from the server device 106. The service information may be bio information related user interest information or useful information. For example, service information may include health related service information provided based on bio information, health schedule management information according to bio information accumulation, bio information based patient management information, and bio information based diet management information.

The SIM card 924 may be a card including a subscriber identification module and may be inserted into a slot formed at a specific position of an electronic device. The SIM card 924 may include unique identification information (e.g., an integrated circuit card identifier (ICCID)) or subscriber information (e.g., an international mobile subscriber identity (IMSI)).

The memory 930 (e.g., the memory 130) may include an internal memory 932 or an external memory 934. The internal memory 932 may include at least one of a volatile memory (e.g., dynamic RAM (DRAM), static RAM (SRAM), synchronous dynamic RAM (SDRAM)) and a non-volatile memory (e.g., one time programmable ROM (OTPROM), programmable ROM (PROM), erasable and programmable ROM (EPROM), electrically erasable and programmable ROM (EEPROM), mask ROM, flash ROM, NAND flash memory, and NOR flash memory).

According to an embodiment of the present disclosure, the internal memory 932 may be a Solid State Drive (SSD). The external memory 934 may further include flash drive, for example, compact flash (CF), secure digital (SD), micro Micro-SD, Mini-SD, extreme digital (xD), or a memory-stick. The external memory 934 may be functionally connected to the electronic device 900 through various interfaces. According to an embodiment of the present disclosure, the electronic device 900 may further include a storage device (or a storage medium) such as a hard drive.

According to various embodiments, the memory 930 may store at least part of collected bio information. For example, the memory 930 may store user-specific or phone number-specific bio information. Alternatively, the memory 930 may store bio information relating to a time point at which lock is released or a point at which security information is inputted normally. The memory 930 may store a list or graph generated by accumulating stored bio information.

The sensor module 940 measures physical quantities or detects an operating state of the electronic device 900, thereby converting the measured or detected information into electrical signals. The sensor module 940 may include at least one of a gesture sensor 940A, a gyro sensor 940B, a barometric pressure sensor 940C, a magnetic sensor 940D, an acceleration sensor 940E, a grip sensor 940F, a proximity sensor 940G, a color sensor 940H (e.g., a red, green, blue (RGB) sensor), a biometric sensor 940I, a temperature/humidity sensor 940J, an illumination sensor 940K, and an ultra violet (UV) sensor 940M. Additionally or alternatively, the sensor module 940 may include an E-nose sensor (not shown), an electromyography (EMG) sensor, an electroencephalogram (EEG) sensor (not shown), an electrocardiogram (ECG) sensor (not shown), an infra red (IR) sensor (not shown), an iris sensor (not shown), or a fingerprint sensor (not shown). The sensor module 940 may further include a control circuit for controlling at least one sensor therein.

At least one sensor of the sensor modules 940 may be used in relation to trigger signal detection. Alternatively, at least one sensor of the sensor modules 940 may be used in relation to user finger detection. Alternatively, at least one sensor of the sensor modules 940 may be used in relation to the detection of bio information (e.g., heart rate information).

The input device 950 may include a touch panel 952, a (digital) pen sensor 954, a key 956, or an ultrasonic input device 958. The touch panel 952 may recognize a touch input through at least one of capacitive, resistive, infrared, or ultrasonic methods, for example. Additionally, the touch panel 952 may further include a control circuit. In the case of the capacitive method, both direct touch and proximity recognition are possible. The touch panel 952 may further include a tactile layer. In this case, the touch panel 952 may provide a tactile response to a user.

The (digital) pen sensor 954 may be implemented through a method similar or identical to that of receiving a user's touch input or an additional sheet for recognition. The key 956 may include a physical button, a touch key, an optical key, or a keypad, for example. The ultrasonic input device 958, as a device checking data by detecting sound waves through a microphone (e.g., a microphone 988) in the electronic device 900, may provide wireless recognition through an input tool generating ultrasonic signals. According to an embodiment, the electronic device 900 may receive a user input from an external device (e.g., a computer or a server) connected to the electronic device 900 through the communication module 920.

The display 960 (e.g., the display 150) may include a panel 962, a hologram device 964, or a projector 966. The panel 962 may include a liquid-crystal display (LCD) or an active-matrix organic light-emitting diode (AM-OLED). The panel 962 may be implemented to be flexible, transparent, or wearable, for example. The panel 962 and the touch panel 952 may be configured with one module. The hologram 964 may show three-dimensional images in the air by using the interference of light. The projector 966 may display an image by projecting light on a screen. The screen, for example, may be placed inside or outside the electronic device 900. According to an embodiment, the display 960 may further include a control circuit for controlling the panel 962, the hologram device 964, or the projector 966.

According to various embodiments, the display 960 may display various information relating to bio information collection. Additionally, the display 960 may display collected bio information. Additionally, the display 960 may display bio information related service information.

The interface 970 may include a high-definition multimedia interface (HDMI) 972, a universal serial bus (USB) 974, an optical interface 976, or a D-subminiature (sub) 978, for example. The interface 970 may be included in the communication interface 160 shown in FIG. 2, for example. Additionally/alternately, the interface 970 may include a mobile high-definition link (MHL) interface, a secure Digital (SD) card/multi-media card (MMC) interface, or an infrared data association (IrDA) standard interface.

The audio module 980 may convert sound into electrical signals and convert electrical signals into sounds. At least some components of the audio module 980 may be included in the input/output interface 140 shown in FIG. 2, for example. The audio module 980 may process sound information inputted/outputted through a speaker 982, a receiver 984, an earphone 986, or a microphone 988. According to various embodiments, the audio module 980 may output bio information related audio information.

The camera module 991, as a device for capturing a still image and a video, may include at least one image sensor (e.g., a front sensor or a rear sensor), a lens (not shown), an image signal processor (ISP) (not shown), or a flash (not shown) (e.g., an LED or a xenon lamp).

The power management module 995 may manage the power of the electronic device 900. Although not shown in the drawings, the power management module 995 may include a power management IC (PMIC), a charger IC, or a battery or fuel gauge, for example.

The PMIC may be built in an IC or SoC semiconductor, for example. A charging method may be classified into a wired method and a wireless method. The charger IC may charge a battery and may prevent overvoltage or overcurrent flow from a charger. According to an embodiment, the charger IC may include a charger IC for at least one of a wired charging method and a wireless charging method. As the wireless charging method, for example, there is a magnetic resonance method, a magnetic induction method, or an electromagnetic method. An additional circuit for wireless charging, for example, a circuit such as a coil loop, a resonant circuit, or a rectifier circuit, may be added.

The battery gauge may measure the remaining amount of the battery 996, or a voltage, current, or temperature of the battery 396 during charging. The battery 996 may store or generate electricity and may supply power to the electronic device 900 by using the stored or generated electricity. The battery 996, for example, may include a rechargeable battery or a solar battery.

The indicator 997 may display a specific state of the electronic device 900 or part thereof (e.g., the AP 910), for example, a booting state, a message state, or a charging state. The motor 998 may convert electrical signals into mechanical vibration. Although not shown in the drawings, the electronic device 900 may include a processing device (e.g., a GPU) for mobile TV support. A processing device for mobile TV support may process media data according to the standards such as digital multimedia broadcasting (DMB), digital video broadcasting (DVB), or media flow.

An information management method and electronic device disclosed in various embodiments may selectively process a partial management and an entire management of a specific function.

Additionally, various embodiments may easily process the storage and management of information generated according to function management, depending on a user selection.

Additionally, various embodiments may support easy accumulation processing and linkage of information generated according to function management.

Additionally, various embodiments may set a trigger relating to a sensor management in a deactivation state, so that they support to manage the sensor based function performance more promptly, easily, and simply.

Each of the above-mentioned components of the electronic device according to various embodiments of the present disclosure may be configured with at least one component and the name of a corresponding component may vary according to the kind of an electronic device. An electronic device according to various embodiments of the present disclosure may include at least one of the above-mentioned components, may not include some of the above-mentioned components, or may further include another component. Additionally, some of components in an electronic device according to various embodiments of the present disclosure are configured as one entity, so that functions of previous corresponding components are performed identically.

The term "module" used in various embodiments of the present disclosure, for example, may mean a unit including a combination of at least one of hardware, software, and firmware. The term "module" and the term "unit", "logic", "logical block", "component", or "circuit" may be interchangeably used. A "module" may be a minimum unit or part of an integrally configured component. A "module" may be a minimum unit performing at least one function or part thereof. A "module" may be implemented mechanically or electronically. For example, "module" according to various embodiments of the present disclosure may include at least one of an application-specific integrated circuit (ASIC) chip performing certain operations, field-programmable gate arrays (FPGAs), or a programmable-logic device, all of which are known or to be developed in the future.

According to various embodiments, at least part of a device (e.g., modules or functions thereof) or a method (e.g., operations) according to this disclosure, for example, as in a form of a programming module, may be implemented using an instruction stored in computer-readable storage media. When at least one processor (e.g., the processor 120) executes an instruction, it may perform a function corresponding to the instruction. The non-transitory computer-readable storage media may include the memory 130, for example. At least part of a programming module may be implemented (e.g., executed) by the processor 120, for example. At least part of a programming module may include a module, a program, a routine, sets of instructions, or a process to perform at least one function, for example.

According to various embodiments, computer recording media are stored, as in the form of a programming module, in computer computer-readable storage media, and the programming module includes an instruction executed by at least one processor, and the instruction may be designed for receiving a trigger signal relating to sensor activation for supporting bio information collection, collecting bio information on a contacted object by activating the sensor when the trigger signal is detected, and outputting the collected bio information.

The computer-readable storage media may include Magnetic Media such as a hard disk, a floppy disk, and a magnetic tape, Optical Media such as Compact Disc Read Only Memory (CD-ROM) and DVD, Magneto-Optical Media such as Floptical Disk, and a hardware device especially configured to store and perform a program instruction (e.g., a programming module) such as Read Only Memory (ROM), Random Access Memory (RAM), and flash memory. Additionally, a program instruction may include high-level language code executable by a computer using an interpreter in addition to machine code created by a complier. The hardware device may be configured to operate as at least one software module to perform an operation of various embodiments and vice versa.

A module or a programming module according to various embodiments may include at least one of the above-mentioned components, may not include some of the above-mentioned components, or may further include another component. Operations performed by a module, a programming module, or other components according to various embodiments of the present disclosure may be executed through a sequential, parallel, repetitive or heuristic method. Additionally, some operations may be executed in a different order or may be omitted. Or, other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for an electronic device, the method comprising:
   activating a heart rate sensor of the electronic device at a predetermined activation period;
   generating a signal at the predetermined activation period by the heart rate sensor;
   recognizing an object contacting the heart rate sensor using the signal;
   in response to recognizing the object, obtaining via the heart rate sensor a bio information corresponding to the object; and
   outputting the obtained bio information on a touchscreen display of the electronic device,
   wherein the recognizing of the object comprises at least one of:
   receiving a specified touch signal occurrence from a touch sensor disposed in an area adjacent to the heart rate sensor,
   receiving a specified pressure signal occurrence from a barometric pressure sensor disposed in an area adjacent to the heart rate sensor, receiving a contact point connection by a button disposed in an area adjacent to the heart rate sensor, or
receiving a specified proximity signal occurrence from a proximity sensor disposed in an area adjacent to the heart rate sensor.

2. The method according to claim 1, wherein the obtaining of the bio information comprises:
determining whether the object contacting the electronic device is a user body according to the received trigger signal, and
if the contacted object is the user body, obtaining the bio information of the user body.

3. The method according to claim 1, wherein the recognizing of the object comprises detecting whether a change in movement of the electronic device where the heart rate sensor is disposed is a specified movement change.

4. The method according to claim 1, wherein the recognizing of the object comprises detecting whether a direction of a front or a rear of the electronic device is rotated and changed a predetermined number of times in a predetermined direction.

5. The method according to claim 1, further comprising:
receiving an input event relating to a transmission of the bio information; and
transmitting the bio information to an external device by using a communication module of the electronic device.

6. The method according to claim 1, further comprising:
determining a state of an electronic device when the object is recognized; and
maintaining the heart rate sensor to be in an activation state or a deactivation state according to at least one of a display turn-on state of the electronic device or a type of an application being executed in the electronic device.

7. The method according to claim 1, further comprising:
receiving an input event relating to a storage of the bio information; and
storing the bio information corresponding to the input event.

8. The method according to claim 7, further comprising:
when the input event is received, outputting at least one of a security information input window or a lock setting screen.

9. The method according to claim 8, further comprising:
at least one of storing the bio information in a memory or transmitting the bio information to a specified device when specified security information or specified lock release information is inputted.

10. An electronic device comprising:
a heart rate sensor;
a touchscreen display;
a communication module;
a memory storing instructions; and
one or more processors electronically connected to the heart rate sensor, the touchscreen display, the communication module, and the memory, the one or more processors configured to:
control the heart rate sensor to be activated at a predetermined activation period,
control the heart rate sensor to generate a signal at the predetermined activation period,
recognize an object contacting the heart rate sensor using the signal,
in response to recognizing the object, obtain via the heart rate sensor a bio information corresponding to the object, and
control the touchscreen display to output the obtained bio information,
wherein the one or more processors are further configured to recognize the object according to at least one of:
a specified touch signal occurrence from a touch sensor disposed in an area adjacent to the heart rate sensor,
a specified pressure signal occurrence from a barometric pressure sensor disposed in an area adjacent to the heart rate sensor,
a contact point connection by a button disposed in an area adjacent to the heart rate sensor, or
a specified proximity signal occurrence from a proximity sensor disposed in an area adjacent to the heart rate sensor.

11. The device according to claim 10,
wherein the one or more processors are further configured to:
determine whether the object is a user body according to the received trigger signal, and
if the object is the user body, obtain the bio information of the user body.

12. The device according to claim 10, wherein the one or more processors are further configured to recognize the object when the electronic device where the heart rate sensor is disposed has a specified change in movement.

13. The device according to claim 10, wherein the one or more processors are further configured to recognize the object when a direction of at least one of a front or rear of the electronic device is rotated and changed a predetermined number of times in a predetermined direction.

14. The device according to claim 10, wherein, if the object is recognized, the one or more processors are further configured to maintain the heart rate sensor to be in an activation or deactivation state according to at least one of a display turn-on state of the electronic device or a type of an application being execution in the electronic device.

15. The device according to claim 10, wherein the one or more processors are further configured to store the bio information corresponding to an input event relating to a storage of the bio information.

16. The device according to claim 15, wherein, when the input event is received, the one or more processors are further configured to output at least one of a security information input window or a lock setting screen to the touchscreen display.

17. The device according to claim 16, wherein the one or more processors are further configured to store the bio information in a memory or transmit the bio information to a specified device when specified security information or specified lock release information is inputted.

18. The method according to claim 10, wherein the one or more processors are further configured to control the communication module to transmit the bio information to an external device.

* * * * *